(12) United States Patent
Anai

(10) Patent No.: US 9,474,299 B2
(45) Date of Patent: Oct. 25, 2016

(54) MUTATION THAT INCREASES THE OLEIC ACID CONTENT IN SOYBEAN OIL AND RESPONSIBLE GENE THEREOF

(75) Inventor: Toyoaki Anai, Saga (JP)

(73) Assignee: SAGA UNIVERSITY, Saga-shi (JP)

( * ) Notice: Subject to any disclaimer, the term of this patent is extended or adjusted under 35 U.S.C. 154(b) by 856 days.

(21) Appl. No.: 13/379,553

(22) PCT Filed: Jun. 21, 2010

(86) PCT No.: PCT/JP2010/060928
§ 371 (c)(1),
(2), (4) Date: Dec. 20, 2011

(87) PCT Pub. No.: WO2010/150901
PCT Pub. Date: Dec. 29, 2010

(65) Prior Publication Data
US 2012/0102587 A1   Apr. 26, 2012

(30) Foreign Application Priority Data

Jun. 22, 2009 (JP) ................................. 2009-147706

(51) Int. Cl.

| | | |
|---|---|---|
| *A01H 5/10* | (2006.01) | |
| *A23L 1/30* | (2006.01) | |
| *A01H 1/04* | (2006.01) | |
| *A23D 9/00* | (2006.01) | |
| *A23D 9/02* | (2006.01) | |
| *A61K 36/48* | (2006.01) | |
| *C12N 9/02* | (2006.01) | |
| *C12N 15/82* | (2006.01) | |
| *C12Q 1/68* | (2006.01) | |

(52) U.S. Cl.
CPC ............... *A23L 1/3006* (2013.01); *A01H 1/04* (2013.01); *A01H 5/10* (2013.01); *A23D 9/00* (2013.01); *A23D 9/02* (2013.01); *A23K 20/158* (2016.05); *A61K 36/48* (2013.01); *C12N 9/0083* (2013.01); *C12N 15/8247* (2013.01); *C12Q 1/6895* (2013.01); *C12Q 2600/13* (2013.01); *G01N 2333/415* (2013.01); *G01N 2333/90245* (2013.01)

(58) Field of Classification Search
None
See application file for complete search history.

(56) References Cited

U.S. PATENT DOCUMENTS

| 5,981,781 A | 11/1999 | Knowlton |
|---|---|---|
| 2003/0074694 A1* | 4/2003 | Lightner et al. .............. 800/281 |
| 2004/0103450 A1* | 5/2004 | Anai et al. .................... 800/278 |

FOREIGN PATENT DOCUMENTS

| JP | 11-508961 A | 8/1999 |
|---|---|---|
| JP | 2004-000003 A | 1/2004 |
| JP | 2005-530506 A | 10/2005 |
| WO | WO 04/000871 A2 | 12/2003 |
| WO | WO 2011/005998 A1 | 1/2011 |

OTHER PUBLICATIONS

Schlueter et al., "The FAD2 Gene Family of Soybean: Insights into the Structural and Functional Divergence of a Paleopolyploid Genome," The Plant Genome [A Supplement to Crop Science] (Jan. 2007), No. 1, pp. S-14-S-26.
Anai et al., "Two high-oleic-acid soybean mutants, M23 and KK21, have disrupted microsomal omega-6 fatty acid desaturase, encoded by GmFAD2-1a," Breeding Science (2008), vol. 58, pp. 447-452.
Buhr et al., "Ribozyme termination of RNA transcripts down-regulate seed fatty acid genes in transgenic soybean," The Plant Journal (2002), vol. 30, No. 2, pp. 155-163.
Kinney and Knowlton, "Designer oils: the high oleic acid soyben," Genetic Modification in the Food Industry. Blackie, London, pp. 193-213 (1998).
Pham et al., "Mutant alleles of FAD2-1A and FAD2-1B combine to produce soybeans with the high oleic acid seed oil trait," BMC Plant Biology (2010), vol. 10, pp. 195 [online] (URL: http://www.biomedcentral.com/1471-2229/10/195).
Tang et al., "Oleate desaturase enzymes of soybean: evidence of regulation through differential stability and phosphorylation," The Plant Journal (2005), vol. 44, pp. 433-446.

* cited by examiner

*Primary Examiner* — Elizabeth McElwain
(74) *Attorney, Agent, or Firm* — Birch, Stewart, Kolasch & Birch, LLP

(57) ABSTRACT

[Problem]
Providing soybean including oleic acid that will exceed the heretofore developed high-oleic soybean without using gene engineering technology.
[Means to Solve the Problem]
The present invention provides a GmFAD2-1b gene loss of function mutation and a type of soybean that includes a GmGAD2-1b gene loss of function mutation.

6 Claims, 6 Drawing Sheets

Super High-Oleic Acid Line-1
(GmFAD2-1a and GmFAD2-1b genes are mutated)

High-Oleic Acid Line-2
(Only GmFAD2-1a is mutated)

MUTATION THAT INCREASES THE OLEIC ACID CONTENT IN SOYBEAN OIL AND RESPONSIBLE GENE THEREOF

TECHNICAL FIELD

The present invention relates to soybean seed in which a loss of function mutation has been introduced to the soybean GmFAD2-1b gene and the gene into which said mutation has been introduced.

BACKGROUND ART

Soybean is the vegetable oil source produced in the greatest quantity worldwide. Since the composition of fatty acids contained in plant oil has a direct effect on the quality of the oil, modification of the composition of fatty acids is a crucial part of breeding, even in soybean. As regards fatty acid composition, generally, if saturated fatty acid content is high, oil quality will be stable. However, ingesting this sort of oil increases the level of low density lipoprotein cholesterol in the blood and is therefore not nutritionally preferable. Further, the polyunsaturated fatty acids like linoleic acid are problematic because they easily oxygenate, are unstable, and easily produce sludge when used as a biofuel.

As in the past, hydrogenation is practiced as a means of stabilizing polyunsaturated fatty acids. This method is, however, not economic because of the costs incurred. Hydrogenation is also not preferable because it produces trans-fatty acids which are believed to lead to risk of coronary disease as a by-product. In contrast, since monounsaturated fatty acids such as oleic acids are comparatively stable to oxidation and lower the blood cholesterol level, soybean rich in oleic acid is preferable both as a source of fuel and as a source of nutrition.

Generally, since the composition of the fatty acid obtained from generally distributed soybean seeds has an oleic acid content of 20 to 25% and a linoleic acid content of 50 to 57%, breeding was undertaken in order to increase the oleic acid content. However, products developed until the present do not contain a practically adequate content of oleic acid.

According to research conducted until the present, in order to increase oleic acid content in vegetable oil, it is reported that it is crucial to reduce the activity of endoplasmic reticulum omega-6 fatty acid desaturase (FAD2), which catalyzes the linoleic acid production process (nonpatent literature 1) by desaturating oleic acid. Therefore, the FAD2 gene that encodes this enzyme is a target during breeding. As FAD2 genetically-modified soybean for which gene modification technology is used, ultrahigh oleic acid soybean (line name: 260-05) in which the expression of the FAD2 gene is suppressed by the co-suppression method has been developed, being reported that oleic acid content has increased to approximately 80% or higher (patent literature 1 and non-patent literature 2). Further, studies of increasing oleic acid content have been reported (patent literature 2) in which the expression of the gene that encodes palmitoyl-ACP thioesterase, which is involved in adjusting the ratio of saturated fatty acid to unsaturated fatty acid, is reduced by genetic modification. However, since these high oleic acid soybean were genetically modified, they were finally rejected by consumers and are not being produced at the present for the purpose of food production.

Accordingly, when the purpose is to provide soybean or soybean oil that contains high oleic acid for consumption, it is preferable to provide high oleic acid soybean without using genetic engineering techniques. In the past, the present inventor prepared 2 types of mutant soybean, namely M23 and KK21, in which the functions of the GmFAD2-1a genes, one of the FAD2 genes, are completely destroyed by inducing mutation and in so doing succeeded in increasing the oleic acid content from approximately 25% to 50% or higher (patent literature 3 and nonpatent literature 1). However, it was difficult to increase the oleic acid content further without using genetic modification.

PRIOR ART DOCUMENTS

Patent Literature

[Patent Literature 1] Japanese National-phase PCT Laid-Open Patent Publication No. JP 1999 11-508961

[Patent Literature 2] Japanese Laid-Open Patent Publication (unexamined patent publication) No. JP 2005-530506

[Patent Literature 3] Japanese Laid-Open Patent Publication (unexamined patent publication) No. JP 2004-3

Non-Patent Literature

[Non-patent Literature 1] Anai et al., Breeding Science 58: 447-452 (2008)

[Non-patent Literature 2] Kinney and Knowlton., Genetic Modification in the Food Industry. Blackie, London. 193-213.pp. (1998)

DISCLOSURE OF THE INVENTION

Problem to be Solved

The problem of the invention is the provision of non genetically-modified soybean that contains oleic acid in a quantity greater than that of the high oleic-acid containing soybean developed until the present.

Means to Solve the Problem

As the result of extensive study towards solving the aforementioned problem, the present inventor has succeeded in inserting a loss of function mutation into GmFAD2-1b, a FAD2 gene different than the wild type soybean GmFAD2-1a gene. In addition, the present inventor discovered that when this mutation-having soybean also has a GmFAD2-1a gene loss of function mutation, oleic acid is not converted into linoleic acid and an extremely high oleic acid content is yielded, therefore completed the present invention.

In other words, the present invention is as stated below.

{1} A non genetically-modified soybean plant having a high oleic acid content wherein loss of function mutations are introduced into both GmFAD2-1a and GmFAD2-1b genes each encoding a ω-6 fatty acid desaturase.

{2} The soybean plant according to {1}, wherein the oleic acid content is 75% or more to the whole fatty acid content.

{3} The soybean plant according to {1}, comprising at least one of following features (a) to (e):
  (a) the soybean plant has a less number of wrinkled seeds compared to the wild type;
  (b) the soybean plant does not substantially produce linoleic acid;
  (c) the soybean plant has a beta-conglycinin content to the total storage protein amount that is not substantially reduced compared to that of the wild type;

(d) the soybean plant has a total storage protein amount that is not substantially reduced compared to that of the wild type;

(e) the fertility of the soybean plant is not lowered compared to that of the wild type.

{4} The soybean plant according to {1}, wherein said loss of function mutation is one selected from the group consisting of missense mutation, a nonsense mutation, a frame-shift mutation, and a null mutation.

{5} The soybean plant according to {1}, wherein said loss of function mutation of GmFAD2-1b gene is one occurs in a codon(s) encoding an amino acid residue included in a region selected from the group consisting of following (1) to (8) of the amino acid sequence of the ω-6 fatty acid desaturase:

(1) a region consisting of the $58^{th}$ to $79^{th}$ amino acid residues (2) a region consisting of the $88^{th}$ to $108^{th}$ amino acid residues (3) a region consisting of the $180^{th}$ to $194^{th}$ amino acid residues (4) a region consisting of the $229^{th}$ to $251^{st}$ amino acid residues (5) a region consisting of the $254^{th}$ to $277^{th}$ amino acid residues (6) a region consisting of the $109^{th}$ to $114^{th}$ amino acid residues (7) a region consisting of the $141^{st}$ to $149^{th}$ amino acid residues (8) a region consisting of the $319^{th}$ to $326^{th}$ amino acid residues {6} The soybean plant according to {5}, wherein said amino acid residue is the $103^{rd}$ and/or $189^{th}$ amino acid residues.

{7} The soybean plant according to {5}, wherein said mutation is a missense mutation of the codon encoding the $103^{rd}$ and/or $189^{th}$ amino acid residues.

{8} The soybean plant according to {7}, wherein the missense mutation of the codon encoding the $103^{rd}$ amino acid residue is caused by a substitution of codon for glycine with one for valine.

{9} The soybean plant according to {7}, wherein the missense mutation the codon encoding the $189^{th}$ amino acid residue is caused by a substitution of codon for threonine with one for proline.

{10} The soybean plant according to {5}, having a gene that has a basic sequence of SEQ ID NO: 3 or 5.

{11} The soybean plant according to {2}, wherein the loss of function mutation of the GmFAD2-1a gene is identical to that of the GmFAD2-1a gene of M23 or KK21 line.

{12} A non genetically-modified soybean plant having a high oleic acid content which can be obtained by cross-mating KK21 line having a depository No. FERM BP-11249 and B12 line having a depository No. FERM BP-11248.

{13} A pharmaceutical composition, food product, or feed comprising the soybean plant recited in any one of {1} to {12}, or the processed material of said plant.

{14} Soybean oil extracted from the soybean plant recited in any one of {1} to {12} or the processed material of said plant.

{15} A pharmaceutical composition, food product, or feed comprising the soybean oil recited in {14}.

{16} Fuel generated from the soybean plant recited in any one of {1} to {12} or the processed material of said plant.

{17} A method for manufacturing a non genetically-modified soybean plant having a high oleic acid content wherein the soybean plant recited in any one of {1} to {12} is cross-mated with one another or another variety of soybean plant.

{18} A method for manufacturing a non genetically-modified soybean plant having a high oleic acid content comprising any of the step selected from the group consisting of the following (i) to (iv):

(i) cross-mating a soybean plant having a mutation in GmFAD2-1a gene with a soybean plant having a mutation in GmFAD2-1b gene;

(ii) subjecting a soybean plant having a mutation in GmFAD2-1a gene to mutagenic agent treatment or X-ray irradiation to induce a loss of function mutation in GmFAD2-1b gene;

(iii) subjecting a soybean plant having a mutation in GmFAD2-1b gene to mutagenic agent treatment or X-ray irradiation to induce a loss of function mutation in GmFAD2-1a gene; or (iv) subjecting a wild type soybean plant to mutagenic agent treatment or X-ray irradiation to induce loss of function mutations in GmFAD2-1b and GmFAD2-1a genes.

{19} A method for screening a non genetically-modified soybean plant having a high oleic acid content comprising steps of:

(a) carrying out amplification of and/or hybridization to the GmFAD2-1a or GmFAD2-1b gene of the subject soybean plant using an oligonucleotide probe including the basic sequence of the mutation site of the GmFAD2-1a or GmFAD2-1b gene of the soybean plant recited in any one of {1} to {12}, and/or an oligonucleotide primer(s) designed as to amplify at least one of the basic sequence of said gene or the complementary sequence thereof so that the amplified fragment includes said mutation site; and (b) detecting the mutation site of said gene.

{20} An oligonucleotide produced so that the basic sequence of the mutation site of the GmFAD2-1a or GmFAD2-1b gene of the soybean plant recited in any one of {1} to {12} is included therein.

{21} The oligonucleotide according to {20} designed so that said mutation site of the GmFAD2-1a or GmFAD2-1b gene is located in the 5' terminal, 3' terminal or center portion of said oligonucleotide.

{22} The oligonucleotide according to {20} or {21} having a length of 10 to 200 bases.

{23} A microarray, wherein the oligonucleotide recited in any one of {20} to {22} is fixed to a support structure.

{24} A kit for detecting a loss of function mutation of GmFAD2-1 a or GmFAD2-1b gene comprising the oligonucleotide recited in any one of {20} to {22} and/or the microarray recited in {23}.

Effect of the Invention

A soybean plant having the mutant gene of the present invention has a high content of oleic acid. Especially when the plant has loss of function mutations in both the GmFAD2-1a and GmFAD2-1b genes, the plant has an extremely high oleic acid content of as much as approximately 80%. This oleic acid value is thought to completely satisfy the desired standard value of oleic acid content. Furthermore, since the super high oleic acid-containing soybean of the present invention is non genetically-modified soybean that can be obtained without the use of genetic modification technology, it is believed that it will have a wide variety of uses and applications as a foodstuff, feed, and a medicinal ingredient without encountering any consumer resistance.

Further, the mutant gene of the present invention can be detected easily through the use of probes and primers made using the oligonucleotides. Therefore, when the soybean of the present invention is crossed with a different soybean type, a high oleic soybeana type having new characteristics can be produced from the genome DNA of the descendant soybean by selecting a soybean line that includes the mutant gene of the present invention by using these probes or primers.

MODE FOR CARRYING OUT THE INVENTION

Figure 1:
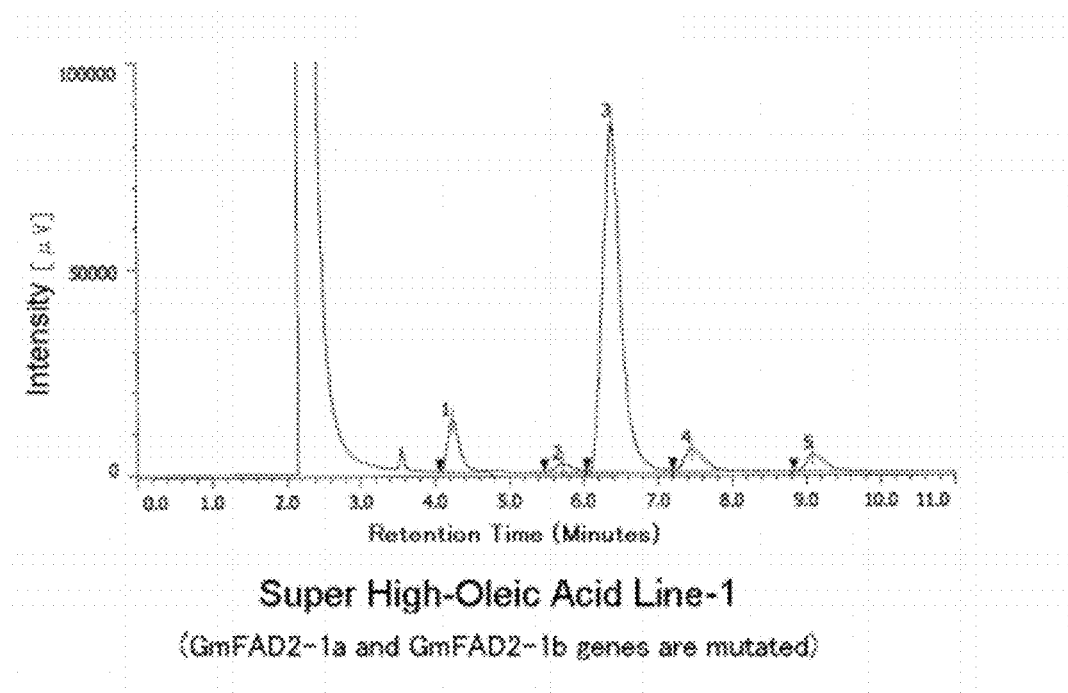
FIG. 1 is of gas chromatography showing the fatty acid composition of seeds of a FH00ES04E11 line having a loss of function mutation in GmFAD2-1 a and GmFAD2-1 b. Peaks 1 to 5 correspond to palmitic acid, stearic acid, oleic acid, linoleic acid, and α-linolenate, respectively.

Hereinbelow the present invention is explained in detail. The embodiments or modes as described below are not intended to limit the scope of the present invention but merely provides exemplary aspects of the present inventions for the purpose of explanation. The present invention may be performed in a variety of embodiments unless it deviates from the scope or spirit thereof.

All articles and patent literatures including patent application publications and patent publications are incorporated herewith by referencing thereto.

The present application also incorporates the disclosure of the specification and figures of Japanese Patent Application No. 2009-147760 having a filing date of 22 Jun. 2009, to which the present invention claims its priority.

The present inventors performed mutagenesis treatment on a soybean line having a loss of function mutation in the GmFAD2-1a gene, succeeded in introducing a loss of function mutation into the GmFAD2-1b gene, and, as a, produced a non-genetically modified soybean plant having loss of function mutations in both the GmFAD2-1b and GmFAD2-1a genes. The present inventors also discovered that the non-genetically modified soybean plant has a high oleic acid content. Further, the present inventors conducted an extensive observation of the non-genetically modified soybean plant obtained by the present invention and discovered that the soybean plant comprises at least one of the following features, i.e. morphologies, (a) to (e):

(a) the number of seeds with wrinkle on the surface thereof is not increased compared to the wild type;

(b) the soybean plant does not substantially produce a problematic amount of linoleic acid;

(c) the soybean plant has a beta-conglycinin content to the total storage protein amount that is not substantially reduced compared to that of the wild type;

(d) the soybean plant has a total storage protein amount that is not substantially reduced compared to that of the wild type;

(e) the fertility of the soybean plant is not lowered compared to that of the wild type.

Accordingly the present invention provides a soybean plant having the mutations as described above, and preferably, a non-genetically modified soybean plant comprising at least one of the above features (a) to (e) (hereinafter referred to as "the soybean plant of the present invention").

As used herein, "a soybean plant" or "soybean" means the individual of the soybean plant in whole or in part, and, in addition to the plant, may also mean an organ of the plant (seed, etc.) cells derived from the plant, or partial structures such as organella.

As used herein, "non genetically-modified soybean plant" means soybeana breeding that has not been subjected to alteration of genetic modification through genetic engineering, in other words, an original line of soybean or varieties obtained through breed improvement by the introduction of genetic mutation without genetic engineering technologies to the original line.

As used herein, "wild type" or "wild type soybean plant" refers to any existing non genetically modified soybean plants which produce ω-6 fatty acid desaturase by possessing normal biological functions. The examples of the wild type soybean plant includes "Bay", "Murayutaka" and "Fukuyutaka", however, not limited thereto.

Among the morphological features as described above, feature (a) means that the ratio of "seeds without wrinkle on its surface" to the total number of soybean seeds harvested from a single soybean plant accounts to 60% or more, 65% or more, 70% or more, 75% or more, or 80% or more, preferably, 81% or more, 82% or more, 83% or more, 84% or more, 85% or more, 86% or more, 87% or more, 88% or more, 89% or more, 90% or more, 91% or more, 92% or more, 93% or more, 94% or more or 95% or more. This feature can be confirmed by macroscopic observation of soybean seeds.

Regarding feature (b), the term "the soybean plant does not substantially produce a problematic amount of linoleic acid" means that the soybean plant does not produce enough linoleic acid to reach a level where the oxidation of oil is accelerated and the stability of the oil is lowered by linoleic acid.

Specifically, feature (b) as described above means that the ratio of linoleic acid to the total fatty acid amount, i.e. the linoleic acid content, is 50% or less, 45% or less, 40% or less, 35% or less, 30% or less, 25% or less, 20% or less, 15% or less, 10% or less, 9% or less, 8% or less, 7% or less, 6% or less, 5% or less, or 4% or less.

The linoleic acid content can be measured through ordinary fatty acid analysis of the fatty acid extracted from the soybean; specifically, the measurement can be performed via gas chromatography analysis under the conditions described in published literatures such as Anai et al., Breeding Science 58: 447-452 (2008), however, measurement procedure should not be limited thereto. Feature (b) as described can be confirmed by measuring the linoleic acid content in the seed of the soybean plant according to the present invention.

Feature (c) as described above means that the beta-conglycinin content as a part of the total storage protein amount of the soybean plant according to the present invention is substantially comparable to or exceeds the ratio of beta-conglycinin content to the entire storage protein amount of the wild type soybean plant. For example, the beta-conglycinin content to the entire storage protein amount of the soybean plant of the present invention is 70% or more, preferably, 75% or more, 80% or more, 85% or more, 90% or more, 91% or more, 92% or more, 93% or more, 94% or more, 95% or more, 96% or more, 97% or more, 98% or more, or 99% or more of the ratio of beta-conglycinin content to the entire storage protein amount of the wild type soybean plant.

The beta-conglycinin content can be measured through ordinary protein analysis of the proteins included in the soybean plant, preferably, the soybean seed. For example, the beta-conglycinin content can be measured by a variety of methods such as sodium dodecyl sulfate polyacrylamide gel electrophoresis (SDS-PAGE), Western blotting, enzyme linked immunosorbent assay (ELISA) and a variety of types of chromatographic analysis. Feature (c) can be confirmed by comparing the thus measured beta conglycinin content of the soybean plant of the present invention with that of the wild type soybean plant.

Feature (d) as described above means that the protein amount contained in the soybean plant of the present invention is substantially comparable to or exceeds the protein amount contained in the wild type soybean plant. For example, the protein amount contained in the soybean plant of the present invention is 70% or more, preferably, 75% or more, 80% or more, 85% or more, 90% or more, 91% or more, 92% or more, 93% or more, 94% or more, 95% or more, 96% or more, 97% or more, 98% or more, or 99% or more of the total protein content of the wild type soybean plant. The protein amount contained in the soybean plant, preferably in the soybean seed, can be measured by the methods as mentioned in the above description of feature (c). Feature (d) can be confirmed by comparing the thus measured protein amount of the soybean plant of the present invention with that of the wild type soybean plant.

Feature (e) as described above means that the fertilization ratio upon pollination by cross mating the soybean plants of the present invention with one another is substantially comparable to or exceeds that obtained by cross mating the wild type soybean plants with one another. As used herein, the term "substantially comparable to or exceeding" means that the fertilization ratio upon pollination between the soybean plants of the invention is 70% or more, preferably, 75% or more, 80% or more, 85% or more, 90% or more, 91% or more, 92% or more, 93% or more, 94% or more, 95% or more, 96% or more, 97% or more, 98% or more, or 99% or more of the fertilization ratio upon pollination between the wild type soybean plants. The fertilization ratio upon pollination can be calculated as the ratio of the number of bean pods formed through artificial pollination by contacting the soybean stamen of the pistil, to the number of soybean flowers subjected to the pollination. Feature (e) can be confirmed by comparing the thus calculated fertilization ratio of the soybean plant of the present invention with that of the wild type soybean plant.

Further, the soybean of the present invention is characterized by its high oleic acid content. For example, the oleic acid content of the soybean of the present invention is 30% or more of the total fatty acid content, preferably, 50% or more, more preferably, 70% or more, 71% or more, 72% or more, 73% or more, 74% or more, 75% or more, 76% or more, 77% or more, 78% or more, 79% or more, 80% or more, or 81% or more, still more preferably, 81.5% or more, and still further more preferably, 81.6% or more. The oleic acid content can be measured through ordinary fatty acid analysis of the fatty acid extracted from the soybean; specifically, the measurement can be performed via gas chromatography analysis under the conditions described in published literatures such as Anai et al., Breeding Science 58: 447-452 (2008), however, it should not limited thereto.

Mutant Genes

The soybean plant of the present invention preferably comprises loss of function mutations in the GmFAD2-1b gene and/or GmFAD2-1a gene. As used herein, "comprising a mutant gene" means that the soybean plant has a mutant gene within its cells. These types of soybean preferably have the mutant gene within the genome of the soybean and more preferably are non genetically-modified soybean that, for example, have the mutant gene in the genome as the result of mutation or crossbreeding with another variety and not as the result of genetic modification.

In soybean that has a loss of function mutation in the GmFAD2-1b gene, comprehensive FAD2 activity within the seed is greatly decreased. In particular, in soybean that has loss of function mutations in both the GmFAD2-1a gene and the GmFAD2-1b gene, FAD2 function inside the seed is almost completely lost, and consequently oleic acid is not converted to linoleic acid.

As used herein, the "GmFAD2-1a gene" and the "GmFAD2-1b" gene are both genes that encode microsomal ω-6 fatty acid desaturase (FAD2) of soybean (Glycine max (L.) Merr.). Further, "gene that encodes ω-6 fatty acid desaturase" means a genetic region consisting of the nucleotide sequence that encodes the amino acid sequence of the ω-6 fatty acid desaturase, i.e., the open reading frame of the ω-6 fatty acid desaturase. An "open reading frame (ORF)" is a DNA or RNA region which is translated into protein and located between the start codon and the stop codon.

ω-6 fatty acid desaturase is an enzyme that catalyzes the reaction in soybean whereby oleic acid is converted to linoleic acid. Although some of the genes confirmed to encode this enzyme are GmFAD2-1a, GmFAD2-1b, GmFAD2-2a, GmFAD2-2b, and GmFAD2-2c, of these, only GmFAD2-1a and GmFAD2-1b are known to be specifically-expressed in seeds in the developmental stage (Anai et al., Breeding Science 58: 447-452 (2008)). GmFAD2-1a and GmFAD2-1b are genes which are located on linkage groups of LGO and LGI respectively, and have base sequences registered as GenBank Accession No. AB188250.1 and AB188251.1. GmFAD2-1a and GmFAD2-1b exhibit 94% homology with respect to their ORF sequence and include amino acids in which 5 residues are different.

The nucleotide sequence of the GmFAD2-1b gene that encodes the Fukuyutaka-derived wild type ω-6 fatty acid desaturase is shown in SEQ ID NO: 1, while the amino acid sequence of the enzyme is shown in SEQ ID NO: 2. Further, the nucleoid sequence of the Fukuyutaka-derived wild type GmFAD2-1a gene is shown in SEQ ID NO: 14, while the amino acid sequence of the wild type GmFAD2-1a enzyme is shown in SEQ ID NO: 15.

As used herein, "a loss of function mutation" means a mutation such that a protein, etc. encoded by the gene loses its biological function. Although this may be either an amorph, in which function is totally lost or a hypomorph, in which function is partially lost, an amorph is preferable since FAD2 function is completely absent. Further, genotype may be either homozygous or heterozygous, but the homozygous is preferable. As used herein, a complete loss of function means that the function of FAD2 is substantially not detectable. For example, if wild type function activity is stipulated as 100% and the mutant is 10% or less, the above means exhibition of function activity of preferably 5% or less, more preferably 3% or less, even more preferably 1% or less and most preferably 0.1% or less. Further, a partial loss of function means that, compared to wild type, the mutant exhibits 90% or less, preferably 70% or less, more preferably 60% or less, even more preferably 50%, still more preferably 40% or less and most preferably 30% or less of function activity.

The loss of function mutation gene of the GmFAD2-1b or GmFAD2-1a gene is not particularly limited as long as the FAD2 encoded by the GmFAD2-1b or GmFAD2-1 a gene loses the FAD2 activity thereof. Preferably, the loss of function mutation gene has an mutation inserted into the GmFAD2-1b or GmFAD2-1a that encodes FAD2, said mutation being selected from the following group: missense mutation, nonsense mutation, frame shift mutation and null mutation.

In a preferably embodiment, said loss of function mutation of GmFAD2-1b gene is one occurs in a codon(s) encoding an amino acid residue included in a region selected from the group consisting of following (1) to (8) of the amino acid sequence of the ω-6 fatty acid desaturase:

(1) a region consisting of the 58$^{th}$ to 79$^{th}$ amino acid residues (2) a region consisting of the 88$^{th}$ to 108$^{th}$ amino acid residues (3) a region consisting of the 180$^{th}$ to 194$^{th}$ amino acid residues (4) a region consisting of the 229$^{th}$ to 251$^{st}$ amino acid residues (5) a region consisting of the 254$^{th}$ to 277$^{th}$ amino acid residues (6) a region consisting of the 109$^{th}$ to 114$^{th}$ amino acid residues (7) a region consisting of the 141$^{4}$ to 149$^{th}$ amino acid residues (8) a region consisting of the 319$^{th}$ to 326$^{th}$ amino acid residues In the above embodiment, the amino acid sequence of said FAD2 protein is one indicated as SEQ ID NO: 2, wherein the amino acid sequences of regions (1) to (8) of the amino acid sequence of SEQ ID NO:2 are as follows:

```
(1) 58th to 79th amino acid residues:
                                        (SEQ ID NO: 16)
Leu Ser Tyr Val Val Tyr Asp Leu Ser Leu Ala Phe Ile Phe Tyr Ile Ala Thr Thr Tyr Phe His (2) 88th to 108th amino acid residues:
                                        (SEQ ID NO: 17)
Ile Ala Trp Pro Ile Tyr Trp Val Leu Gln Gly Cys Ile Leu Thr Gly Val Trp Val Ile Ala (3) 180th to 194th amino acid residues:
                                        (SEQ ID NO: 18)
Leu Gly Arg Ala Ala Ser Leu Leu Ile Thr Leu Thr Ile Gly Trp
```

```
(4) 229th to 251St amino acid residues:
                                        (SEQ ID NO: 19)
Ile Tyr Val Ser Asp Val Ala Leu Phe Ser Val Thr Tyr Leu Leu Tyr Arg Val Ala Thr Met Lys Gly (5) 254th to 277th amino acid residues:
                                        (SEQ ID NO: 20)
Trp Leu Leu Cys Val Tyr Gly Val Pro Leu Leu Ile Val Asn Gly Phe Leu Val Thr Ile Thr Tyr Leu Gln (6) 109th to 114th amino acid residues:
                                        (SEQ ID NO: 21)
His Glu Cys Gly His His (7) 141st to 149th amino acid residues:
                                        (SEQ ID NO: 22)
Trp Lys Ile Ser His Arg Arg His His (8) 319th to 326th amino acid residues:
                                        (SEQ ID NO: 23)
His Val Ala His His Leu Phe Ser
```

Among regions (1) to (8) as listed above, the regions defined in (1) to (5) are included in the transmembrane domain of FAD2 protein whereas those defined in (6) to (8) are included in the histidine box of FAD2 protein. The transmembrane dmain is an important component for stabilizing the structure of FAD2 protein whereas the histidine box is a binding site for metal ions, and is therefore an important component for the activation of the FAD2 enzyme. As such, the occurrence of a mutation in any of these regions would cause the FAD2 enzyme to lose its activity. Preferably, said mutation occurs in any one of the amino acid regions (1) to (3) among regions (1) to (8).

The loss of function mutation that occurs in the soybean of the present invention may be any of the following: a missense mutation, a nonsense mutation, a frame-shift mutation, a null mutation or a combination thereof. Nevertheless, in a embodiment in which the mutation occurs in a codon(s) encoding an amino acid residue included in a region selected from the group consisting of (1) to (8) as described above, the mutation is preferably a missense mutation. Examples of amino acid substitution which may be caused by the missense mutation include a substitution of a hydrophilic amino acid residue with a hydrophobic amino acid and a substitution of a hydrophobic amino acid residue with a hydrophilic amino acid. Examples of the hydrophilic amino acid residue include Gly, Thr, Ser, Tyr, Cys, Gln and Asn whereas examples of the hydrophobic amino acid residue include Val, Pro, Leu, Trp, Leu, Phe, Ala, Met and Ile.

More preferably, the mutation in the GmFAD2-1b gene is the missense mutation of the codon that encodes the 103$^{rd}$ or 189$^{th}$ amino acid residue of the amino acid sequences of ω-6 fatty acid desaturase. For example, the aforementioned missense mutation in the 103$^{rd}$ amino acid residue is caused by a substitution from a glycine codon to a codon for the 19 types of amino acid other than glycine (Ala, Arg, Asn, Asp, Cys, Gln, Glu, His, Ile, Leu, Lys, Met, Phe, Pro, Ser, Thr, Trp, Tyr, Val). More preferably, the mutation is caused by a substitution from a glycine codon (GGT, GGC, GGA, GGG) to a valine codon (GTT, GTC, GTA, GTG). Preferably, the aforementioned missense mutation in the 189$^{th}$ amino acid is caused by a substitution from a threonine codon to a codon for the 19 types of amino acid other than threonine (Ala, Arg, Asn, Asp, Cys, Gln, Glu, His, Ile, Leu, Lys, Met, Phe, Pro, Ser, Gly, Trp, Tyr, Val). Even more preferably, said missense mutation is due to a substitution from a threonine codon (ACT, ACC, ACA, ACG) to a proline codon (CCT, CCC, CCA, CCG). Alternatively, combinations of the aforementioned $103^{rd}$ amino acid mutation and $189^{th}$ amino acid mutation are also included.

Most preferable is the loss of function mutation gene of the GmFAD2-1b gene having a base sequence shown in SEQ ID NO: 3 or SEQ ID NO: 5. SEQ ID NO: 3 shows the basic sequence of loss of function mutation type GmFAD2-1b gene in which the guanine base (G) at position 308 of the basic sequence as shown in SEQ ID NO: 1 is substituted with thymine (T). By the above substitution, the FAD protein encoded by the base sequence of SEQ ID NO: 3 has the amino acid sequence as shown in SEQ ID NO: 4 in which the glycine residue at position 103 of the amino acid sequence of the wild type FAD (as shown in SEQ ID NO: 2) is substituted to valine. SEQ ID NO:5 shows the basic sequence of loss of function mutation type GmFAD2-1b gene in which the adenine base (A) at position 565 of the basic sequence as shown in SEQ ID NO:1 is substituted with cytosine (C). By the above substitution, the FAD protein encoded by the base sequence of SEQ ID NO: 5 has the amino acid sequence as shown in SEQ ID NO: 6 in which the threonine residue at position 189 of the amino acid sequence of the wild type FAD (as shown in SEQ ID NO: 2) is substituted to proline.

As used herein, "FAD2 activity" means an activity to catalyze the reaction in which oleic acid is converted to linoleic acid in soybean cells, preferably soybean seed cells.

The $103^{rd}$ and $189^{th}$ amino acid residues of the amino acid sequences of ω-6 fatty acid desaturase are the $103^{rd}$ and $189^{th}$ amino acid residues, respectively, when counted in order from the carboxyl terminal with the methionine encoded as the start codon of the GmFAD2-1b being designated as the $1^{st}$ amino acid residue. Accordingly, the codons that encode the $103^{rd}$ and $189^{th}$ amino acid residues in the amino acid sequence of ω-6 fatty acid desaturase mean the codons consisting of, respectively, nucleotides at positions 307 to 309 and the nucleotides at positions 565 to 567 with the nucleotide located at the 5' terminal of the open reading frame of GmFAD2-1b stipulated as the first nucleotide.

As used herein a "missense mutation" means a change in the type of an amino acid due to the change or substitution of a base in the corresponding codon of the nucleic acid sequence.

As used herein, a "nonsense mutation" means a mutation wherein the codon changes into a stop codon due to change or substitution of the codon and, from said codon onward, the 3' side of the ORF region becomes untranslated. Nonsense mutations are also called stop mutations.

As used herein, a "frame shift mutation" means a mutation wherein the reading frame of codons at the 3' side of the region is altered due to the insertion or deletion of a base(s).

As used herein, a "null mutation" means a mutation wherein the nucleotide sequence that encodes the protein thereof is completely deleted or for which the functional protein cannot be expressed even if the nucleotide sequence exists.

Further, in a wild type FAD2 amino acid sequence (SEQ ID NO: 2), the $103^{rd}$ amino acid residue is glycine. In one aspect of the present invention, FAD2 activity is lost through the inclusion of a missense mutation in the $103^{rd}$ amino acid residue of the FAD2 amino acid sequence. Especially if the $103^{th}$ amino acid residue (glycine) is substituted with one of the 19 amino acids other than glycine, for example valine (SEQ ID NO: 4) due to said missense mutation, or more specifically, if the codon that corresponds to the $103^{rd}$ amino acid of FAD2 is "GTC" (SEQ ID NO: 3), the GmFAD2-1b gene will become unable to generate functional FAD2.

Further, in the amino acid sequence of wild type FAD2 (SEQ ID NO: 2), the $189^{th}$ amino acid residue is threonine. In one aspect of the present invention, FAD2 activity is lost through the inclusion of a missense mutation in the $189^{th}$ amino acid residue of the FAD2 amino acid sequence. Especially if the $189^{th}$ amino acid residue (threonine) is substituted with one of the 19 amino acids other than threonine, for example proline (SEQ ID NO: 6) due to said missense mutation, or more specifically, if the codon that corresponds to the $189^{th}$ amino acid of FAD2 is "CCA" (SEQ ID NO: 5), the GmFAD2-1b gene will become unable to generate functional FAD2.

In other words, if the $308^{th}$ nucleotide residue of the wild type GmFAD2-1b gene as shown in SEQ ID NO: 1 has Single Nucleotide Polymorphism (SNP) in which guanine is substituted with thymine (SEQ ID NO: 3), or if there is SNP in which the adenine in the $565^{th}$ nucleotide is substituted with cytosine (SEQ ID NO: 5), then the $103^{rd}$ amino acid residue of FAD2 is substituted from glycine to valine or the $189^{th}$ amino acid is substituted from threonine to proline, therefore the GmFAD2-1b that comes from this kind of sequence can be said to be a loss of function mutation gene. In the present invention as long as the function of the FAD2 encoded by the GmFAD2-1b gene is lost, the nucleotide may be mutated by loss, insertion, or substitution in nucleotide sequences other than positions 308 and 565 thereof. In other words, the GmFAD2-1b gene of the soybean plant of the present invention may have a nucleotide sequence which hybridize to the nucleotide consisting of a base sequence complementary to the base sequence shown in SEQ ID NOs: 3 and 5 under stringent conditions, and encode a protein having FAD2 activity. Preferably the nucleotide sequence of the loss of function mutant of the GmFAD2-1b gene has 85% or more homology to the sequence shown in SEQ ID NO: 3 or SEQ ID NO: 5; more preferable is 90% or greater homology; even more preferable is 95% or greater homology; still more preferable is 98% or greater homology, and most preferable is 99% or greater homology. Any genes having such mutations are also included in the scope of the invention.

The base sequence as shown in SEQ ID NO: 3 is a FH00ES04E11 line-derived mutant-type GmFAD2-1b nucleotide sequence having a mutation in which guanine of $308^{th}$ nucleotide of the wild type GmFAD2-1b gene shown in SEQ ID NO: 1 is converted to thymine. By contrast, the base sequence as shown in SEQ ID NO: 5 is an E015B12 line-derived mutant type GmFAD2-1b gene nucleotide sequence having a mutation in which adenine of $565^{th}$ nucleotide of the wild type GmFAD2-1b gene shown in SEQ ID NO: 1 is converted to cytosine.

"Stringent conditions" are, for example, conditions having a salt (natrium, etc.) concentration of 150 to 900 nM and a temperature of 55 to 75° C., preferably, a salt (natrium, etc.) concentration of 250 to 450 nM and a temperature of 62 to 70° C.

As used herein, "protein having FAD2 activity" and "functional FAD2" means a protein having activity identical to endoplasmic reticulum omega-6 fatty acid desaturase (FAD2) that catalyzes the reaction that converts oleic acid into linoleic acid inside soybean cells, preferably soybean seed cells. Accordingly, "not expressing protein having FAD2 activity" means as a result that protein having FAD2 activity is not produced or the protein having FAD2 activity is not expressed for a reason such as the nucleotide sequence that encodes said protein does not exist, the nucleotide that encodes the amino acid sequence of the domain having the aforementioned catalyst function of the protein does not exist, the nucleotide sequence that encodes the aforementioned protein exists but said nucleotide sequence is not transcribed, or the messenger RNA (mRNA) which is the transcription product of the nucleotide sequence that encodes the aforementioned protein is not translated, etc.

FAD activity can be measured using, for example, yeast *Saccharomyces cerevisiae* (*S. cerevisiae*). *S cerevisiae* has no capability for synthesizing polyunsaturated fatty acids such as linoleic acid. Therefore, in S. cerevisiae cells, the quantity of the linoleic acid obtained by recombining and expressing the target GmFAD2-1b gene is measured as the activity quantity of the FAD2 encoded by GmFAD2-1b. Details on FAD activity measurements performed using S. cerevisiae are described in Anai, T et al. (Plant Science, 106, 1615-1623 (2005)) and can be applied to the present invention.

Regarding the homology between 2 or more types of nucleotide sequence and amino acid sequence, one sequence is stipulated as the reference sequence (for example, the sequence shown in SEQ ID NO.: 3 or 5) among the target sequence, and measurements can be taken by aligning other sequences against this reference sequence. This kind of alignment can be performed using a multiple alignment algorithm, and computer software that uses such an algorithm is available in ClustalW, etc., which are available from the European Bioinformatics Institute: EBI.

The GmFAD2-1b gene loss of function mutation in soybean varieties such as Bay, OLERICHI50, and Fukuyutaka can be obtained by performing X-ray irradiation or treatment with a mutagenic agent such as methanesulfonic acid ethyl ester (EMS) in accordance with usual methodology. For example, when a mutation is being introduced via X-ray irradiation, a mutation can be introduced by irradiating dry seed at a dose level of 100 Gy to 300 Gy. Further, when performing EMS processing, a mutation can be introduced by performing EMS exposure using EMS at 0.1 weight % to 0.5 weight % concentration for 30 minutes to 24 hours. Treatment with EMS at the above level makes it possible to voluntarily introduce a mutation into a target region while minimizing a possible influence on the genes adjacent to the GmFAD2-1b gene.

It is preferable for the soybean of the present invention to have a loss of function mutation in the GmFAD2-1 a gene in addition to a loss of function mutation in the GmFAD2-1b gene. As genes that encode FAD2 expressed inside the seed, only GmFAD2-1a and GmFAD2-1b have been identified. If both these genes lose their functions, the oleic acid to linoleic acid conversion in the soybean seeds will decline precipitously, resulting in a significant increase in the oleic acid content.

In the present invention, a "loss of function mutation gene of the GmFAD2-1a gene" is not especially limited if the FAD2 encoded by GmFAD2-1a loses its functionality, but is preferably a loss of function mutation gene in which a mutation selected from the group consisting of a missense mutation, a nonsense mutation, a frame shift mutation and a null mutation has been introduced into the GmFAD2-1a gene. More preferably the GmFAD2-1a loss of function mutation is identical to a GmFAD2-1a gene mutation of M23 or KK21 line. Most preferably, the GmFAD2-1a loss of function mutation is identical to that of M23 line.

"Missense mutations", "nonsense mutations", "frameshift mutations", and "null mutations" are as explained above.

In the present invention, a "GmFAD2-1a gene mutation of M23 line" includes a mutation in the GmFAD2-1a of the M23 soybean described in Anai et al., Breeding Science 58: 447-452 (2008). For the detection of this mutation, the following primers, which are designed to amplify the nucleic acid sequence including the ORF region of the GmFAD2-1a gene of Bay, the parental variety of M23:

(SEQ ID NO: 7)
5'-attgatagccctccgttcccaaga-3'

(SEQ ID NO: 8)
5'-atacacacaaagtcattacgcggcaa-3' can be used to perform a polymerase chain reaction (PCR). When agarose gel electrophoresis is performed on the thus obtained PCR product, the approximately 1.3 Kpb band, which should be detected when the parental variety genome DNA is used as a template strand, becomes undetectable when the M23 genome DNA is used as a template strand. The foregoing is a mutation in which the entirety of the nucleotides of the ORF for the wild type GmFAD2-1a was deleted. (See JP 2004-3 and Anai et al., Breeding Science 58: 447-452 (2008)). See the following for information on PCR and agarose gel electrophoreses: Sambrook, Fritsch and Maniatis, "Molecular Cloning: A Laboratory Manual" 2nd Edition (1989), Cold Spring Harbor Laboratory Press.

In the present invention, the "GmFAD2-1a gene mutation of KK21 line" includes a frame shift mutation of the GmFAD2-1a gene of the KK21 gene detailed in Anai et al., Breeding Science 58: 447-452 (2008). The KK21 mutation reportedly exhibits the same effects as the M23 mutation (Anai et al., Breeding Science 58: 447-452 (2008)). Specifically, this means that the 232" thymine base of the ORF of the wild type GmFAD2-1a gene (SEQ ID NO: 14) is deleted and there is a mutation in which frame shift occurs in the region of the 3' side from the deletion site. For the detection of this mutation, for example, the following primer sets:

(SEQ ID NO: 9)
5'-attgatagccctccgttcccaaga-3'

(SEQ ID NO: 10)
5'-attgtgagtgtgacgagaagagaaac-3' can be used, a PCR reaction is induced, a portion of the base sequence of GmFAD2-1a is amplified, a purified DNA fragment is used as a template and the following primer: 5'-gggtctagcaaaggaaacaacaatgggaggt-3' (SEQ ID NO: 11) is used to perform sequencing, and the loss of the $232^{nd}$ thymine base of the ORF can be confirmed. For information on the sequencing method, see Sambrook, Fritsch and Maniatis, "Molecular Cloning: A Laboratory Manual" 2nd Edition (1989), Cold Spring Harbor Laboratory Press.

The activity of the FAD2 encoded by the GmFAD2-1a gene, like the activity of FAD2 encoded by the GmFAD2-1b gene, can be measured through use of the yeast S. cerevisiae (see Anai, T et al. (Plant Science, 106, 1615-1623 (2005)).

The loss of function mutation of the GmFAD2-1a gene, like the loss of function mutation for the GmFAD2-1b gene, can be obtained by subjecting soybean varieties such as Bay, Murayutaka, and Fukuyutaka. etc. to x-ray irradiation or treatment with a mutagenic agent such as EMS.

Method of Producing the Soybean Plant of the Invention

The soybean plant of the present invention can be produced by performing any of the step selected from the group consisting of the following (i) to (iv):

(i) cross-mating a soybean plant having a mutation in GmFAD2-1 a gene with a soybean plant having a mutation in GmFAD2-1b gene;

(ii) subjecting a soybean plant having a mutation in GmFAD2-1a gene to mutagenic agent treatment or X-ray irradiation to induce a loss of function mutation in GmFAD2-1b gene;

(iii) subjecting a soybean plant having a mutation in GmFAD2-1b gene to mutagenic agent treatment or X-ray irradiation to induce a loss of function mutation in GmFAD2-1a gene; or (iv) subjecting a wild type soybean plant to mutagenic agent treatment or X-ray irradiation to induce loss of function mutations in GmFAD2-1b and GmFAD2-1a genes.

Figure 8:
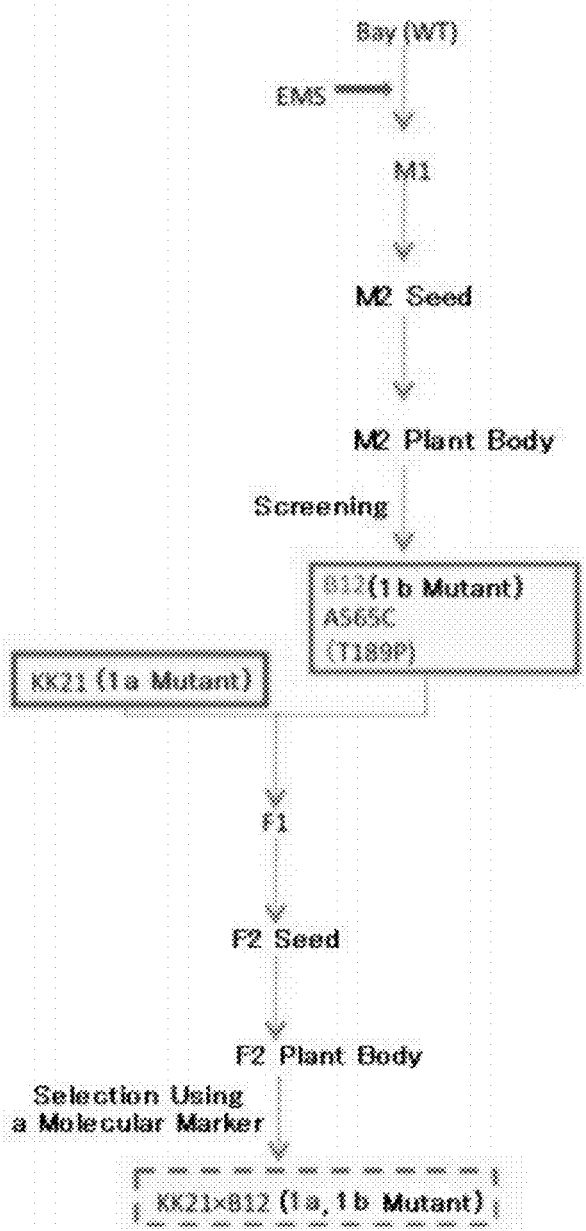
FIG. 8 illustrates a method of producing the soybean plant of the present invention.

One embodiment of step (i) as described above is illustrated in FIG. 8. In the method shown in FIG. 8, KK21 line, a soybean line having a GmFAD2-1a gene mutation, is cross-mated with B12, a soybean line having a GmFAD2-1b gene mutation, thereby producing a soybean plant having a super high oleic acid content. Note that the soybean line that can be used in step (i) is not limited soybean lines having a GmFAD2-1a gene mutation or soybean lines having a GmFAD2-1b gene mutation.

One embodiment of step (ii) as described above is illustrated in FIG. 9. In the method shown in FIG. 9, BC3F4 line, which is a soybean line having a GmFAD2-1 a gene mutation, is subjected to EMS treatment, thereby producing a soybean plant having a super high oleic acid content. Note that the soybean line that can be used in step (ii) is not limited to soybean lines having a GmFAD2-1a gene mutation.

Figure 9:
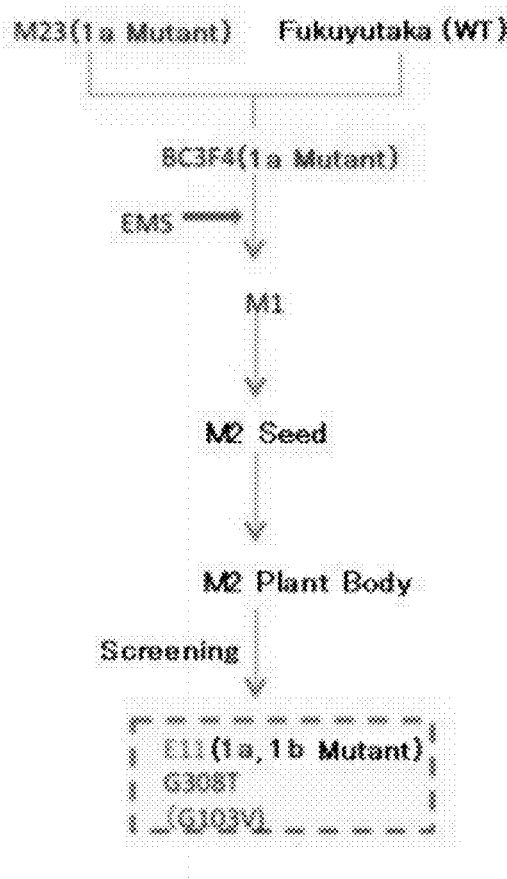
FIG. 9 illustrates a method of producing the soybean plant of the present invention.

Examples of step (iii) as described above includes the same method as illustrated in FIG. 9 with the proviso that soybean lines having a GmFAD2-1a gene mutation are replaced with soybean lines having a GmFAD2-1b gene mutation such as B12 or E11. Note that the soybean line that can be used in step (iii) is not limited to a soybean line having a GmFAD2-1b gene mutation.

The above step (iv) describes a method of producing a soybean plant having a super high oleic acid content is produced by subjecting a wild type soybean plant such as Fukuyutaka to EMS treatment to induce loss of function mutations in both the GmFAD2-1b and GmFAD2-1a genes. Note that the wild type soybean line that can be used in step (iv) is not limited to Fukuyutaka.

Examples of the GmFAD2-1 a gene mutant soybean line includes OLERICHI50, M23 and KK21 whereas examples of the GmFAD2-1 b gene mutant soybean line include E015B12 and FH00ES04E11 (hereinafter referred to as "B12" and "E11", respectively). Among the aforementioned soybean lines, KK21 and B12 were deposited in the International Patent Organism Depositary (IPOD) (AIST Tsukuba Central 6, 1-1-1 Higashi, Tsukuba, Ibaraki 305-8561 Japan) on 22 Apr. 2010, with the depository numbers of "FERM BP-11249" and "FERM BP-11248", respectively.

Note that the seeds of M23, KK21, B12, KK21×B12 and E11 lines are also preserved at the Faculty of Agriculture, Saga University (1 Honjo-machi, Saga-city, Saga 840-8502 Japan).

Uses

As used herein, "pharmaceutical composition" means items used to diagnose, treat, or prevent the target disease when administered to targets such as humans or animals; quasi drugs can only be included if a similar effect can be obtained therefrom. Isoflavone contained in soybean is known for exhibiting an agonistic effect to the estrogen receptors, and can also be used as a drug to combat osteoporosis. Further, since the soybean of the present invention contains oleic acid in abundance, for drugs that contain the soybean of the present invention or a processed material thereof, the use of oleic acid to lower the level of cholesterol in the blood can be considered in addition to the conventional properties of soybean. Examples of the medical conditions that can be targeted by these medicines are hyperlipidemia, arteriosclerosis, and diabetes, etc.

A "soybean product" is a product obtained after, for example, treating with a certain enzyme, powderizing, drying, heating, freezing, or refining the soybean plant of the invention.

As used herein, the term "foodstuffs" means items consumed either for the obtainment of nutrients or for pleasure. Soybean has long been consumed as a foodstuff. The soybean plant of the present invention can be eaten as a raw foodstuff like edamame, eaten as a fermented food like natto, or consumed as a processed food like dried beans, miso, soybean sauce, tofu, dried bean curd, soybean milk, or toasted soybean flour. Since the soybean of the present invention is obtainable as non-genetically modified soybean, it is expected that consumer resistance to its use in foods/drinks will be low. Further, since the soybean of the present invention contains abundant oleic acid, it is expected that consuming it as a foodstuff will lower the level of cholesterol in the blood, thereby effectively preventing lifestyle-related diseases. In addition, the soybean of the present invention can also be used as a supplement, health food, or food for specified health use in order to obtain the aforementioned benefits.

In the present invention, "feed" means material given to domestic animals as food. "Domestic animals" includes animals other than pets such as livestock, domestic fowl, and farm-raised fish. Soybean is widely used in feed for livestock and domestic fowl such as cows, pigs, and chickens as well as in pet food. When the soybean of the present invention is ingested as feed, it can be expected that the high oleic acid content will reduce the level of cholesterol in the blood. It can also be conceived that the soybean of the present invention will contribute to the maintenance and enhancement of the health of domestic animals. In addition, the feed of the present invention is expected to increase the oleic acid content in the meat and eggs of the domestic animals, which may lead to increased health among those who eat the aforementioned meat and eggs.

In the present invention "soybean oil" means the oil obtained from soybean or the processed material thereof. In addition to being used for frying and in salads, soybean is widely used as a raw ingredient in margarine and mayonnaise. Further, in addition to food uses, soybean oil is used as an ink because it is highly transparent. Due to its high oleic acid content, the soybean oil extracted from the soybean of the present invention not only contributes to the good health of those who consume it, but has the superior effect of being highly stable with regard to oxygenation at high temperatures.

Further, since the soybean oil extracted from the soybean of the present invention has a high oleic acid content, it can be used in medical products, foods, or feed materials pursuant to the objective of lowering the level of cholesterol in the blood.

In the present invention, "fuel" means the material which generates energy through a chemical reaction. The fuel of the present invention is not limited as long as the fuel it can be obtained through production with soybean as its basic ingredient, however a preferable example is biodiesel. "Biodiesel" means diesel engine fuel made from biologicallyderived oils. Preparing biodiesel from raw material such as conventional soybean that contains a copious amount of polyunsaturated fatty acid such as linoleic acid presents the problem of easily creating sludge when heated. In contrast, the content of oleic acid, a monounsaturated fatty acid, of the soybean of the present invention is high. Therefore, if biodiesel is prepared therefrom, sludge will not easily be produced, and it is expected that a high-quality biodiesel that is stable with relation to oxidation can be provided. The methods described in "Biodiezeru Nenryo no Seizou/Riyou ni kakaru Gaidorain (Guidelines for Biodiesel Manufacturing and Use)" ((Zenkoku Biodezeru Nenryou Riyou Suishinn Kyougikai) National Biodiesel Fuel Use Promotion Council, May 30, 2008) can be used as manufacturing methods and methods of use for biodiesel fuel.

Cross Breeding

By crossing the soybean species of the present invention with one another or another non genetically-modified species, a new soybean species having characteristics of the soybean of the present invention can be produced. The thus produced soybean also has a high oleic acid content and at least one of the following features (a) to (e):

(a) the number of seeds with wrinkle on the surface thereof is not increased compared to the wild type;

(b) the soybean plant does not substantially produce a problematic amount of linoleic acid;

(c) the soybean plant has a beta-conglycinin content to the total storage protein amount that is not substantially reduced compared to that of the wild type;

(d) the soybean plant has a total storage protein amount that is not substantially reduced compared to that of the wild type;

(e) the fertility of the soybean plant is not lowered compared to that of the wild type.

Preferably, by crossing the soybean species of the present invention with another non genetically-modified species, a new species of non genetically-modified soybean having a loss of function mutation of the GmFAD2-1b gene (and a loss of function mutation of the GmFAD2-1a gene) can be prepared. For example, by crossing the soybean species of the present invention with another non genetically-modified soybean species that has resistance to a specific pest and/or cultivation condition, a new species of non genetically-modified soybean can be prepared with a high oleic acid content and that is resistant to a specific pest and/or cultivation condition.

In the present invention, "cross-mating" or "cross-breeding" means breeding between 2 individuals with a different genetic composition, resulting in the formation of a hybrid. Backcross is the preferred cross breeding method. Since it is necessary to almost completely lose the FAD2 activity encoded by GmFAD2-1b (and GmFAD2-1a) in order to realize high oleic content in the new species of soybean obtained by cross breeding, it is necessary to obtain a homozygote of the GmFAD2-1b gene mutation (and GmFAD2-1a gene mutation) by backcrossing the new soybean species with the soybean species of the present invention. "Backcrossing" is a method wherein the child born between parent A (GmFAD2-1b gene mutant), which has the mutation, and parent B (existing soybean varieties such as Bay and Fukuyutaka), which does not, is bred with parent B (existing soybean varieties such as Bay and Fukuyutaka), mutant GmFAD2-1b is retained, and a descendant with the qualities of parent B is obtained.

Screening Method

Based on the characteristics of the soybean of the present invention such as it preferably having loss of function mutations in GmFAD2-1b and GmFAD2-1a genes, the soybean having a high oleic acid content as described above or the soybean having at least one of features (a) to (e) as described above can be screened by detecting the mutation in either (or both) of the GmFAD2-1b and GmFAD2-1a genes.

One method of detecting loss of function mutation genes of the GmFAD2-1 b or GmFAD2-1a gene of the present invention is a method for detecting a loss of function mutation of the GmFAD2-1b gene comprising steps of:

(a) carrying out amplification of and/or hybridization to the GmFAD2-1a or GmFAD2-1 b gene of the subject soybean plant using an oligonucleotide probe including the basic sequence of the mutation site of the GmFAD2-1a or GmFAD2-1b gene of the soybean plant according to the present invention, and/or an oligonucleotide primer(s) designed as to amplify at least one of the basic sequence of said gene or the complementary sequence thereof so that the amplified fragment includes said mutation site; and (b) detecting the mutation site of said gene.

Some examples of this detection method are methods which are commonly known such as the PCR method, the TaqMan PCR method and the sequence method. In particular, if the loss of function mutation is SNP, some examples are the invader method and the TILLING method, but are not limited to thereto.

If the PCR method is used, it is preferable to prepare a primer that has, in its of its 3' terminal portion, a complementary sequence to the base sequence of the mutation site. By using a primer thusly designed, the primer will completely hybridize to the template, when the sample which is the template exhibits mutation. Therefore the polymerase elongation reaction will progress. In contrast, when the template has no mutation, then the nucleotide at the primer's 3' terminal will cause a mismatch with the template, so that there will be no elongation reaction. Accordingly, when such a primer is used for PCR amplification, and an amplicon with a certain size is detected, then it is determined that the template, which is the sample, has a mutation. When there is no amplification product, it is determined that the template has no mutation. For information on PCR and agarose gel electrophoresis, see: Sambrook, Fritsch and Maniatis, "Molecular Cloning: A Laboratory Manual" 2nd Edition (1989), Cold Spring Harbor Laboratory Press.

The TaqMan PCR method is a method that employs a PCR reaction using fluorescent labeled allele specific oligo and Taq DNA polymerase (Livak, K. J. Genet. Anal. 14, 143 (1999); Morris T. et al., J. Clin. Microbiol. 34, 2933 (1996)).

The sequence method is a method wherein the presence/absence of a mutation is analyzed by amplifying DNA fragments of the region containing the mutation using PCR, and sequencing the DNA sequence using Dye Terminator (Sambrook, Fritsch and Maniatis, "Molecular Cloning: A Laboratory Manual" 2nd Edition (1989), Cold Spring Harbor Laboratory Press).

In DNA microarrays, one end of a nucleotide probe is attached to a support structure in the form of an array. DNA microarrays include DNA chips, gene chips, microchips, and bead arrays. One example of a DNA microarray assay such as a DNA chip is a GeneChip assay (Affymetrix, Inc.; U.S. Pat. Nos. 6,045,996, 5,925,525, and 5,858,659). GeneChip technology uses miniature high-density microarrays of oligonucleotide probes attached to the tip.

The invader method is a method combining hybridization of 2 types of reporter probe which are specific to each of polymorphic allele such as SNP and 1 type of invader probe to the template DNA and DNA cleavage by a Cleavase enzyme having special endonuclease activity to recognize and cleave a certain DNA structure. (Livak, K. J. Biomol. Eng. 14, 143-149 (1999); Morris T. et al., J. Clin. Microbiol. 34, 2933 (1996); Lyamichev, V. et al., Science, 260, 778-783 (1993)) et al.

TILLING (Targeting Induced Local Lesions IN Genomes) method is a method to screen a mismatch pair caused by a mutation included in the genome of the mutant population produced by mutagenesis, by using PCR amplification and CEL I nuclease treatment. According to the TILLING method, by using primer sets such as set forth below, for example, to PCR-amplify an ORF-containing region of the GmFAD2-1b or GmFAD2-1a gene the in the sample and treating the PCR product with CEL I nuclease, the presence of a mutation can be checked.

```
For amplifying GmFAD2-1b gene:
                                    (SEQ ID NO: 12)
5'-tctgtcacttccctccattcattttg-3'

(SEQ ID NO: 13)
5'-gggaagcttatacacaaagtcattacgcggcaa-3'

For amplifying GmFAD2-1a gene:
                                    (SEQ ID NO: 7)
5'-attgatagcccctccgttcccaaga-3'

(SEQ ID NO: 13)
5'-gggaagcttatacacaaagtcattacgcggcaa-3'
```

CEL I nuclease is an end nuclease which specifically cleaves the mismatch site of a double strand DNA. If the sample contains a mutation in the GmFAD2-1b or GmFAD2-1a gene, a mismatch region appears in the above-mentioned PCR product. In contrast, no mismatch region will appear if no mutation is included. Therefore, if there is a mutation, the mismatch pair region of the PCR product is cleaved, whereas if there is no mutation the PCR product is not cleaved. Accordingly, the presence of mutants can be easily confirmed by analyzing CEL I nuclease-processed PCR product with agarose electrophoresis and the like and comparing the length of the nuclear acid sequences. For more specific information on nuclease, see the following source: Oleykowski et al., Nucleic Acids Research, vol. 26, No. 20, 4597-4602 (1998).

In mutation detection methods such as those illustrated above, the oligonucleotide prepared so as to include the loss of function mutation site of the GmFAD2-1b or GmFAD2-1a gene is used as a probe or a primer. Accordingly, the present invention provides an oligonucleotide prepared so as to include the loss of function mutation site of the GmFAD2-1b or GmFAD2-1a gene.

When detecting a loss of function mutation of a GmFAD2-1 b or GmFAD2-1a gene by the invader method, the primer or probe to be used is designed so as to include the SNP site at its 3' or 5' terminal of the base sequence of said primer or the probe, designed so that the SNP site is included at the 3' or 5' terminal of the complementary sequence thereof, or designed so that the SNP site is included within 4 bases from the 3' or 5' terminal of the former (primer or probe, or complementary sequence) or preferably within 2 bases. Alternatively, the primer or probe to be used is designed so that SNP is included in the center of the length of the base sequence of the oligonucleotide. The "center" means the central region such that the number of bases upstream of the SNP base in the direction of the 5' terminal and the number of bases in the 3' terminal direction are substantially identical. When the oligonucleotide base number is odd, the center's 5 bases is preferable, more preferable is the center's 3 bases, and even more preferable is the exact center, which is the 1 base. On the other hand, when the number of oligonucleotide bases is even, the "center" is preferably the 4 bases at the center region and still more preferably the 2 bases in the center region.

Further, when the oligonucleotide of the present invention is used as an allele probe in the invader method, said oligonucleotide is preferably one in which the GmFAD2-1b or GmFAD2-1a gene sequence including the aforementioned loss of function mutation site or the fragment that hybridizes to the complimentary sequence thereof and the fragment that does not hybridize thereto (flap part) are associated though the gene sequence of the aforementioned loss of function mutation site or the complimentary sequence thereof When the oligonucleotide of the present invention is hybridized to the nucleic acid molecule in the sample, the hybridization reaction is carried out under stringent conditions.

It is preferable if the length of the base sequence of the oligonucleotide of the present invention is designed to be at least 10 bases long, more preferably 10 to 200 bases, even more preferably 15 to 150 bases, and most preferably 18 to 80 bases.

This oligonucleotide sequence can be used as a probe to detect the test gene or can be used as either the forward (sense) primer or reverse (antisense) primer.

Oligonucleotide primers or oligonucleotide probes designed as above can be chemically synthesized in accordance with a well-known means or method. However, in general, oligonucleotide primers or oligonucleotide probes are chemically synthesized with a commercially-available device.

Fluorescent labels (for example, FITC, FAM, VIC, Redmond Dye, etc.) and quenchers thereof may be attached to the probes in order to automatize tasks.

Microarray

A microarray can be prepared by affixing one end of the oligonucleotide of the present invention to a support such as those made of glass, silicon, or gel. The oligonucleotide array is produced by, for example, a light irradiation chemical synthesis procedure (Affymetrix, Inc.), which is a combination of a solid chemical synthesis procedure and a photolithography fabrication technique used in the semiconductor industry. By using a photolithography mask in order to specify the boundaries of the chemical reaction site of a chip and by carrying out a specific chemical synthesis step, a high density array with an oligonucleotide probe attached to a prescribed location of the array can be configured.

Kit

In another embodiment of the present invention, a GmFAD2-1b or GmFAD2-1a gene loss of function mutation detection kit including the oligonucleotides of the present invention and a microarray prepared through the use of these oligonucleotides is provided. In addition to the oligonucleotides of the present invention and microarray prepared through the use of these oligonucleotides, this sort of kit may also include a detection reaction solution, a control oligonucleotide, a vessel(s) used for detection reaction, and an instruction booklet.

Hereinbelow, the present invention is explained in more detail through examples. The purpose of these examples is to illustrate the present invention, not to restrict it. The percentages (%) indicated in the examples and comparative examples hereinbelow denote percent by mass.

EXAMPLE

Example 1

Plant Material

The soybean (Glycine max (L.) Merr.) varieties used as material are as below.

(i) Bay;
(ii) OLERICHI50;
(iii) BC3F4 line (variety into which the deletion mutation of the GmFAD2-1a gene was introduced through backcrossing Fukuyutaka with an M23 line)

The seeds of soybean types (i) to (iii) were immersed in an 0.3% EMS aqueous solution overnight, then the soybean M1 seeds obtained by rinsing for 8 hours were sown in a field, and the M1 plant bodies were cultivated in accordance with the usual method. M2 seed was recovered one from each plant whose fertility had been preserved and stored. The following year, the stored M2 seeds were sown in the field again, and M2 plant bodies were cultivated. At this point in time, each harvested M2 plant was given a different line number, DNA was extracted from the green leaves, the adequately aged and dried M3 seeds were recovered from each plant, and said seeds were stored in a freezer at −20° C.

DNA Extraction:

DNA extraction was carried out using a partial modification of the CATB method (Murray and Thompson (1980) Nucleic Acids Res. 8: 4321-4325). Specifically, approximately 100 mg of green leaves was pulverized in liquid nitrogen, 300 µl of 2% CTAB solution (100 mM Tris-HCl (pH8.0), 20 mM EDTA (pH8.0), 1.4 M NaCl, 2% CTAB) was added, the resultant liquid was kept at 65° C. for 30 minutes, the plant residue was precipitated through centrifugal separation, and the supernatant was recovered. The supernatant was deproteinated through chloroform extraction, 1 ml of 1% CTAB solution (50 mM Tris-HCl (pH8.0), 10 mM EDTA (pH8.0), 1% CTAB) was added to the extract, and the DNA-CTAB conjugate was precipitated through centrifugal separation. The obtained precipitate was dissolved in 200 µl of 1 M NaCl containing a final concentration of 5 µg/ml of RNaseA, and combined with 300 µl of 2-propanol and then DNA was precipitated through centrifugal separation. The thus obtained precipitate was suspended in 100 µl of a diatomaceous earth suspension (50 g/l diatomaceous earth, 50 mM Tris-HCl (pH 7.5), 7M guanidine HCl, 10 nM EDTA), and DNA was bonded to the diatomaceous earth. The diatomaceous earth was washed twice in a 70% aqueous ethanol solution and then a ⅟₁₀ concentration TE buffer [1 mM Tris-HCl (pH8.0), 0.2 mM EDTA (pH8.0)] was used to elute the DNA.

Mutant Variant Screening:

A pooled DNA obtained by combining DNAs from eight plants was used as the template and a PCR reaction solution was prepared to contain the following primers specific to the GmFAD2-1b gene and Pfu DNA polymerase:

```
Forward primer:
                                  (SEQ ID NO: 12)
5'-tctgtcacttccctccattcattttg-3'

Reverse primer:
                                  (SEQ ID NO: 13)
5'-gggaagcttatacaaagtcattacgcggcaa-3'
```

Amplification of the target gene region was carried out by repeating the following cycle for 40 rounds: 95° C.: 30 seconds, 65°: 1 minute, 72° C.: 2 minutes.

The obtained PCR product was thermally-denatured at 95° C. for 5 minutes, then cooled to 85° C. at a rate of 2° C./second and kept at 85° C. for 1 minute. Next, the obtained PCR product was cooled to 25° C. at the rate of 0.1° C./second and kept at 25° C. for 1 minute. Finally, the obtained PCR product was cooled to 4° C. at maximum rate and the temperature was maintained.

Next, reaction buffers (5×: 1 M HEPES-NaOH (pH6.5), 50 mM KCl, 15 mM MgCl$_2$, 0.05% Triton X-100) and CEL I nuclease prepared in accordance with Yang et al. (Biochemistry 39: 3533-3541 (2000)) was added, and a DNA fragment having a mismatch was cleaved by warming the above at 37° C. for 10 minutes. Thereafter, an electrophoretic sample buffer containing a final concentration of 0.5% SDS and 1×GelRed solvent was added to quench the reaction, and a mutant variant in which a mutation formed in the target sequence was selected by 1.5% agarose electrophoresis.

Mutation Site Identification:

PCR amplification of the GmFAD2-1b gene was carried out again with the mutant DNA obtained through screening as a template, using the specific primer set utilized in screening (SEQ ID NOs: 12 and 13):

```
                                  (SEQ ID NO: 12)
5'-tctgtcacttccctccattcattttg-3'

(SEQ ID NO: 13)
5'-gggaagcttatacacaaagtcattacgcggcaa-3'
```

The base sequence of the DNA fragments obtained through PCR amplification was identified via the direct sequence method.

Identification Result:

Four lines of mutants having base substitution in GmFAD2-1b gene were obtained from M2 individuals of 8768 lines obtained through EMS-process in total: 3626 lines derived from Bay; 3360 lines derived from OLERICHI50; and 1782 lines derived from BC3F4, which is Fukuyutaka×M23. Of the above, 2 lines had silent mutations not accompanied by a change in amino acids, while it became obvious that in the other 2 systems amino acid substitution was occurring in conjunction with base substitution. Of these, in the Bay-derived mutant "E015B12 line", the 565$^{th}$ base in the base sequence of the GmGAD2-1b gene was substituted from A to C and, as a result, it turned out that the 189$^{th}$ amino acid residue of the amino acid sequence of FAD2 was changed from threonine to proline. In a BC3F4-derived mutant "FH00ES04E11 line", the 308$^{th}$ base in the base sequence of the GmFAD2-1b gene was substituted from G to T and, as a result, it turned out that the 103$^{rd}$ amino acid residue in the amino acid sequence of FAD2 was changed from glycine to valine.

Figure 2:
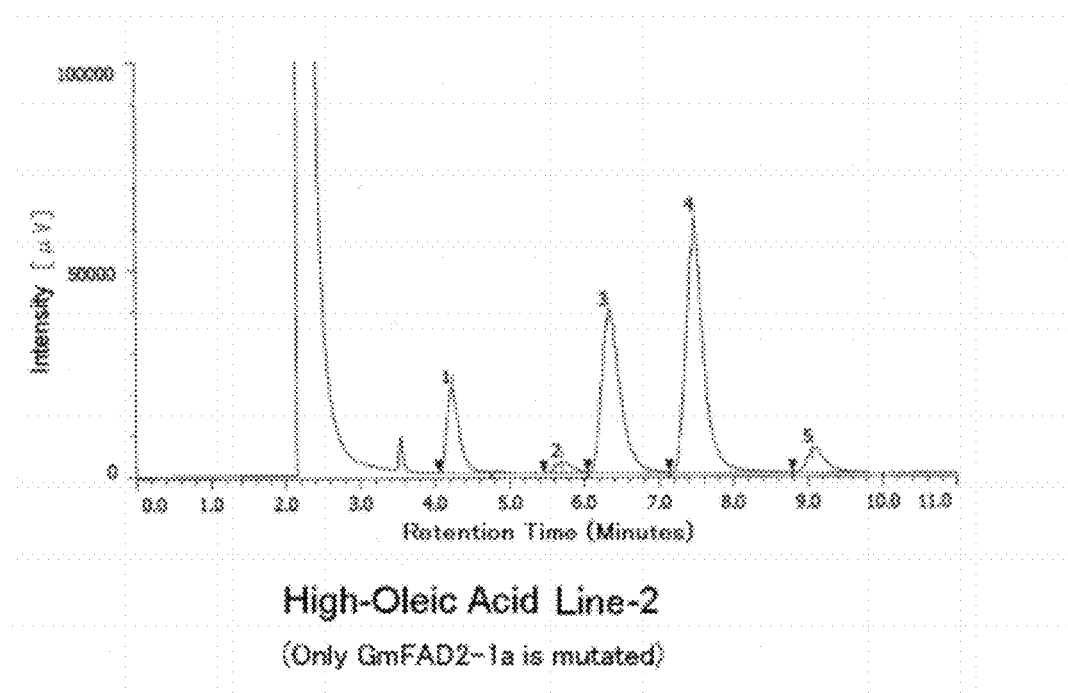
FIG. 2 is of gas chromatography showing the fatty acid composition of seeds of a BC3F4 line having a loss of function mutation in only GmFAD2-1 a. Peaks 1 to 5 correspond to the relationship shown in FIG. 1.
Figure 3:
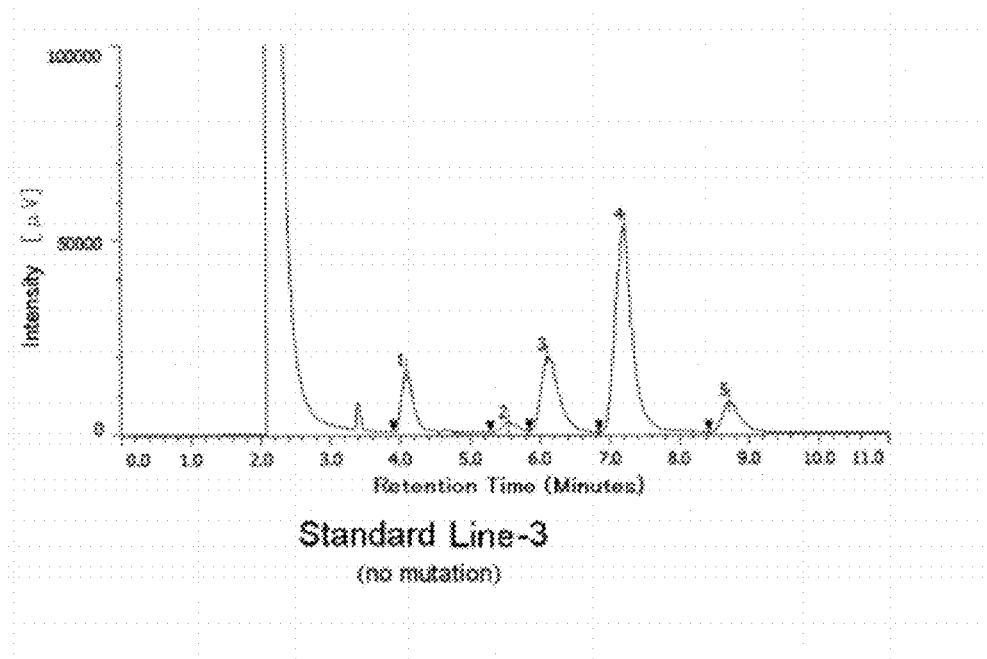
FIG. 3 is of gas chromatography showing the fatty acid composition of Fukuyutaka seeds that do not have a loss of function mutation in GmFAD2-1 a or GmFAD2-1 b. Peaks 1 to 5 correspond to the relationship shown in FIGS. 1 and 2.

Mutant Gene Evaluation:

The mutant genes of the E015B12 line and FH00ES04E11 line, for which change is recognized in the FAD amino acid sequence, were cloned into the yeast expression vector pYES2/CT. Thereafter, yeast expression vectors containing either wild type GmFAD2-1b gene (Fukuyutaka derived), mutant type GmFAD2-1a gene (BC3F4 line derived), or mutant type GmFAD2-1b gene (E015B12 line and FH00ES04E11) were respectively introduced into Saccharomyces cerevisiae (INVSc1 strain), and the expression of the transgene was induced by cultivating the above at 20° C. for 72 hours in SC culture medium that contains 2% galactose and does not contain uracil. Thereafter, fatty acid methyl ester was prepared from the harvested genetically-modified yeast cells and mutant seed powder using the sulfuric acid-methanol method and gas chromatography was used to analyze the fatty acid composition in accordance with the method noted in Non-patent Reference 1. The results of the analysis are shown in FIGS. 1 to 3.

Based on gas chromatography results, the fatty acid composition of soybean containing the wild type GmFAD2-1b, soybean containing the GmFAD2-1a mutant type gene, and soybean containing both the GmFAD2-1b and GmFAD2-1a mutant genes was compared. Comparative results are shown in Table 1.

[Table 1]

TABLE 1

Comparison of Oleic Acid Pigment in Different Strains

| Strain | Palmitic Acid | Stearic Acid | Oleic Acid | Linoleic Acid | α-Linoleic Acid | Mutant Gene |
|---|---|---|---|---|---|---|
| Very High-Oleic Acid Strain-1 | 7.8% | 2.0% | 79.6% | 6.3% | 4.3% | GmFAD2-1a and GmFAD2-1b |
| High-Oleic Acid Strain-2 | 11.5% | 2.4% | 33.3% | 47.8% | 5.0% | GmFAD2-1a only |
| Standard Variety-3 | 11.9% | 2.7% | 20.3% | 56.7% | 8.4% | Fukuyutaka (no mutation) |

The fatty acid composition analysis revealed that the amino acid substitution mutation found in the E015B12 and FH00ES04E11 mutant lines caused a significant decline in the enzymatic activity of the GmFAD2-1b gene product. In particular, it became apparent that enzymatic activity of the product of the mutant GmFAD2-1b gene isolated from the FH00ES04E11 line had declined to such an extent that linoleic acid could not be synthesized (See FIG. 1 and Table 1.).

In addition, it became apparent that the oleic acid content had increased to 79.6% in the FH00ES04E11 line. When compared with the effect of the approximate 13% increase in oleic acid content of the soybean (BC34F line (oleic acid content: 33.3%)) in which a deletion mutation of the GmFAD2-1a gene was introduced into the basic variety Fukuyutaka (oleic acid content: 20.3%), an approximate 46.3% increase in oleic acid content was confirmed between the BC3F4 line and the FH00ES04E 11 line. This result shows that an extraordinarily high effect was obtained.

Example 2

Cross-Mating of the GmFAD2-1b Mutant and the GmFAD2-1a Mutant

The E015B12 line produced in Example 1 was cross-mated with a KK21 line to produce a "KK21×B12" line which has loss of function mutations in both the GmFAD2-1b and GmFAD2-1a genes.

In brief, in the afternoon of the day before cross-mating, a flower bud of the KK21 line which was expected to bloom on the next day was opened and all stamens were carefully removed so as not to damage the pistil. Then, the flower bud was covered with a bag in order to prevent it from drying out and being contaminated with pollen from the outside. Blooming of the B12 line was confirmed during a period from 9 AM to 11 AM on the day cross-mating was performed in order to harvest pollen from flowers which just bloomed on the same day. The thus harvested pollen was applied to the tip of the pistil of the KK21 flower from which the stamen was removed on the day before. The flower was covered with a bag immediately after completion of the cross-mating procedure in order to prevent it from drying out and becoming contaminated with undesirable pollen. The bag was removed two days later.

Selection of Double-Mutant Line

The F1 seed "K21×B12" line obtained by cross-mating as described above was seeded. DNA was extracted from green leaves of the plant budded from the seed and used as a template for PCR to detect mutant genes of GmFAD2-1a and GmFAD2-1b using the following primers:

```
For amplifying GmFAD2-1a mutant gene:
Forward primer:
                                    (SEQ ID NO: 24)
5'-atattacacattcagcaaaacaactga-3'

Reverse primer:
                                    (SEQ ID NO: 13)
5'-gggaagcttatacacaaagtcattacgcggcaa-3'

For amplifying GmFAD2-1b mutant gene:
Forward primer:
                                    (SEQ ID NO: 12)
5'-tctgtcacttccctccattcattttg-3'

Reverse primer:
                                    (SEQ ID NO: 13)
5'-gggaagcttatacacaaagtcattacgcggcaa-3'
```

The PCR was performed under the same reaction conditions as those described in "Mutant Variant Screening", Example 1.

Figure 4:
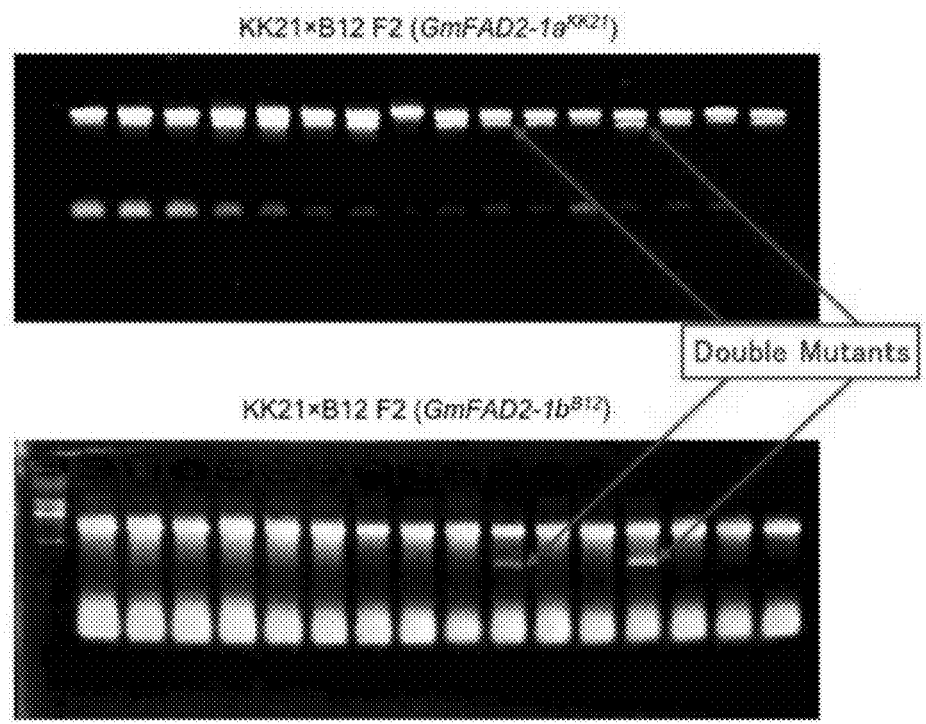
FIG. 4 shows the results of digestion pattern analysis by CEL I nuclease treatment.

Mutant gene detection was performed in accordance with the procedure for "Mutant Variant Screening" as described above. As a result, it was confirmed that the line was heterozygous for the genes originated from KK21 and B12 lines, respectively. The F2 seeds obtained from the F1 plant were seeded in the same manner. Then, to detect mutant genes, DNA was extracted from the green leaves of each plant budded from the seeds. As a result, a double-mutant line was obtained as shown in FIG. 4: The upper panel shows the result for the GmFAD2-1a mutant gene of KK21 origin; the lower panel shows the result for the GmFAD2-1b mutant gene of B12 origin, in which the order of the analyzed samples shown in both panels correspond to each other).

Confirmation of Restriction Digestion Pattern of the Mutant Soybean Plants

Figure 5:
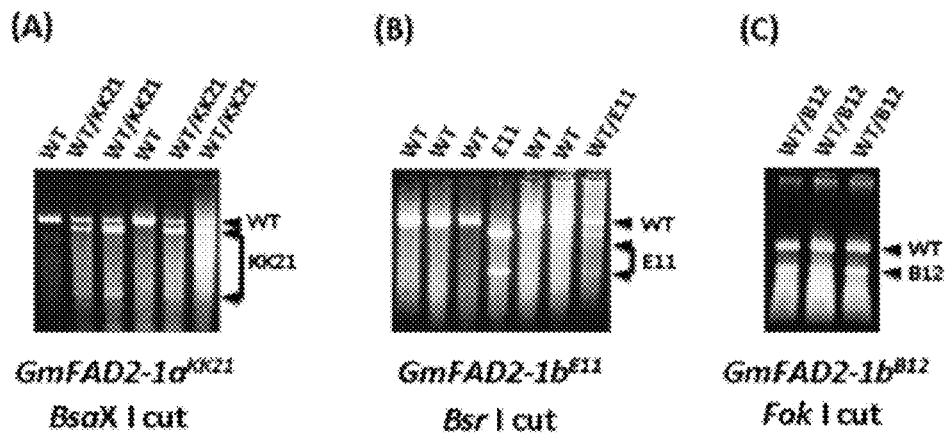
FIG. 5 shows the results of the analysis on restriction enzymatic digestion patterns.

In addition to the method described above, the double-mutant lines can be selected by PCR amplifying the GmFAD2-1a gene of KK21 origin and the GmFAD2-1b gene of B12 or E11 origin, and then detecting the change in the restriction digestion pattern that is specific to the sequence of the mutant gene. In brief, the mutant gene of each line was detected through the procedure as follows:

Panel (A) of FIG. 5 shows the BsaX I restriction pattern of the GmFAD2-1a mutant gene of KK21 origin. The mutant gene is cleaved at one site to form two restriction fragments of approximately 1.0 kbp and 0.3 kbp, respectively, whereas the wild type is not cleaved and maintains its length of approximately 1.3 kbp.

Panel (B) of FIG. 5 shows the Bsr I restriction pattern of the GmFAD2-1b mutant gene of E11 origin. The mutant gene is not cleaved and maintains its length of approximately 1.4 kbp whereas the wild type is cleaved to form two restriction fragments of approximately 1.0 kbp and 0.4 kbp.

Panel (C) of FIG. 5 shows the Fok I restriction pattern of GmFAD2-1b mutant gene of B12 origin. The mutant gene is cleaved to form restriction fragments of approximately 0.7 kbp whereas the wild type is not cleaved and maintains its length of approximately 1.4 kbp.

Protein Composition Analysis of the Mutant Soybean Plants

Protein composition was analyzed by SDS-PAGE for the following soybean lines: Bay and Murayutaka as the wild type lines; and the following as the mutant lines: KK21, B12, KK21×B12, which is a cross-bred line of KK21, B12, and E11. In brief, SDS-PAGE was performed as follows:

Soybean seeds were ground using an electric mill to prepare 10 mg of soybean seed powder. To the powder, 500 µl of sample buffer (100 mM Tris-HCl (pH6.8), 2% SDS, 10% glycerin, 5% 2-mercaptoethanol, 0.1% Bromophenol blue) was added and the resulting mixture was heated at 100° C. for 10 minutes. Then, the mixture was centrifuged at 1500 rpm for 10 minutes and the resulting supernatant was separated by 12.5% SDS-PAGE. The polypeptide bands were visualized by coomassie brilliant blue to compare the results between the lines.

Figure 6:
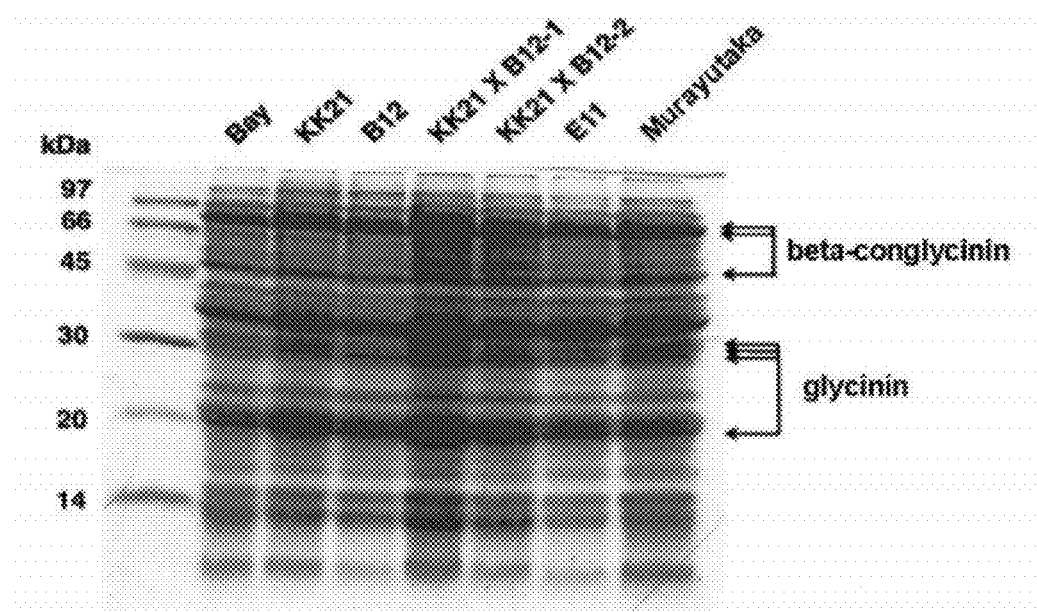
FIG. 6 shows the results of SDS-PAGE analysis on the compositions of the proteins included in the indicated soybean lines.

As shown in FIG. 6, none of the mutant lines (KK21, B12, KK21×B12 and E11) displayed outstanding difference in its protein composition from that of the wild line (Bay and Murayutaka). Further, there was no difference in the content of beta-conglycinin and glycinin, both of which are the major protein components of soybean, between the mutant and wild type lines (FIG. 6).

Fatty Acid Composition Analysis on the Mutant Soybean Plants

Fatty acid composition was analyzed by gas chromatography for the following soybean lines: Bay and Murayutaka as the wild type lines; KK21, B12, KK21×B12 which is a cross-bred line of KK21 and B12, and E11 as the mutant lines. In brief, fatty acid methyl ester was prepared from soybean seed powder of each line by sulfate-methanol treatment and subjected to gas chromatography analysis in accordance with the method described in Anai et al., Breeding Science 58: 447452 (2008). The results are shown in Table 2 and FIG. 7.

Figure 7:
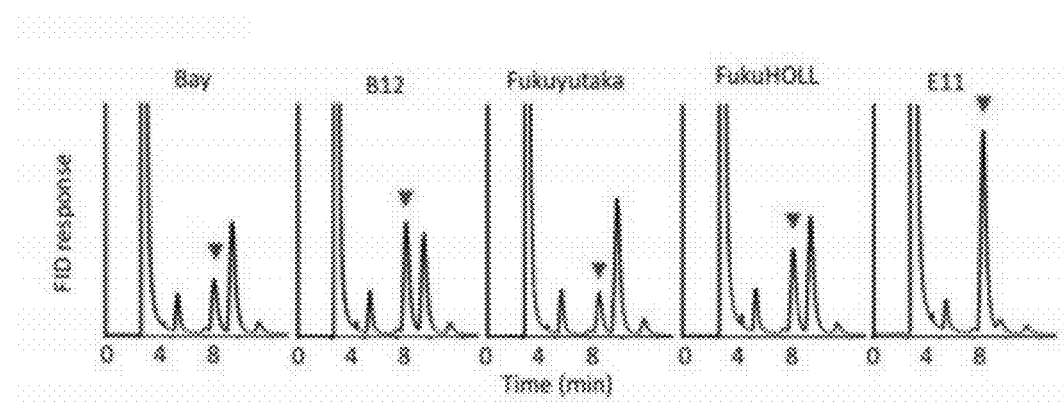
FIG. 7 shows the results of gas-chromatography analysis on the compositions of the fatty acids included in the indicated soybean lines.

No peak for a different type of fatty acid was observed between the mutant and wild type soybean lines (see FIG. 7). With this result, it was confirmed that no different type of fatty acid is produced from the wild type lines upon loss of functions in GmFAD21b gene, GmFAD21a gene, or both of these genes.

Morphological Observation of the Mutant Soybean

The morphology of the soybean seed was microscopically observed for the following lines: Bay as the wild type; M23, KK21 and BC3F4 as the mutant lines for GmFAD2-1a gene; B 12 as the mutant line for GmFAD2-1b gene; and E 11 as the double mutant line for GmFAD2-1a and GmFAD21b genes.

Through the observation of the soybean seed morphologies, it was found that the M23 line and lines having GmFAD21a mutant gene of M23 origin (BC3F4 and E11) have higher ratios of wrinkled soybean seeds to the total number of soybean seeds harvested from a single plant (see Table 3). On the other hand, among the mutant lines, KK21 and B12 lines which do not have GmFAD21 a mutant gene of M23 origin showed ratios of wrinkled soybean seeds comparable to those of the wild type line, Bay (see Table 3).

TABLE 3

| Strain | Total No. of Seeds per Plant | Total No. of Wrinkled Seeds per Plant |
|---|---|---|
| Bay | 139 | 9 |
| M23 | 103 | 33 |
| KK21 | 134 | 8 |
| B12 | 131 | 7 |
| BC3F4 (including M23) | 86 | 21 |
| E11 (including M23) | 83 | 19 |

INDUSTRIAL UTILITY

Through the use of the loss of function mutation gene of the GmFAD21b of the present invention as a marker, soybean having a high oleic acid content can be screened. Further, by using the soybean of the present invention, soybean oil with a high oleic acid content can easily be obtained. By crossing the soybean of the present invention with other varieties, soybean can be produced that has a high oleic acid content in its seeds and also has other characteristics.

TABLE 2

| Line | Fatty acid (% ± SD) | | | | | Genotype | | |
|---|---|---|---|---|---|---|---|---|
| | Palmitate | Stearate | Oleate | Linoleate | Linolenate | GmFAD2-1a | GmFAD2-1b | GmFAD3-1b |
| Bay | 11.9 ± 0.5 | 2.1 ± 0.1 | 27.1 ± 3.2 | 52.7 ± 2.0 | 6.3 ± 0.9 | WT | WT | WT |
| KK21 | 11.4 ± 0.5 | 1.7 ± 0.2 | 47.2 ± 1.3 | 33.2 ± 0.8 | 6.5 ± 0.7 | KK21 | WT | WT |
| B12 | 11.2 ± 0.2 | 1.7 ± 0.1 | 43.2 ± 1.2 | 38.8 ± 0.4 | 5.1 ± 0.6 | WT | B12 | WT |
| KK21 × B12 | 8.7 ± 0.4 | 2.0 ± 0.1 | 81.6 ± 0.5 | 4.2 ± 0.1 | 3.5 ± 0.2 | KK21 | B12 | WT |
| Fukuyutaka | 12.8 ± 0.3 | 2.0 ± 0.1 | 19.3 ± 0.8 | 58.2 ± 0.5 | 7.7 ± 0.1 | WT | WT | WT |
| BC3F4 | 11.6 ± 0.3 | 2.0 ± 0.3 | 33.7 ± 0.8 | 47.9 ± 0.8 | 4.8 ± 0.2 | M23 | WT | M5 |
| E11 | 7.9 ± 0.1 | 1.6 ± 0.3 | 80.7 ± 0.9 | 6.1 ± 0.2 | 3.8 ± 0.6 | M23 | E11 | M5 |

As indicated in Table 2, the oleic acid content of the soybean line comprising loss of function mutations in both GmFAD21b and GmFAD21a genes (KK21×B12 and E11) was found to exceed 80%. This result proves that a soybean plant having a high oleic acid content can be obtained as long as it comprises loss of function mutations in both GmFAD21b and GmFAD21a genes regardless of the original line.

[Depository Numbers]

Depository Information

FERM BP-11248: Deposited to International Patent Organism Depositary (IPOD) (AIST Tsukuba Central 6, 1-1-1 Higashi, Tsukuba, Ibaraki 305-8561 Japan) on 22 Apr. 2010.Line Identification; B12

FERM BP-11249: Deposited to International Patent Organism Depositary (IPOD) (AIST Tsukuba Central 6, 1-1-1 Higashi, Tsukuba, Ibaraki 3058561 Japan) on 22 Apr. 2010.Line Identification; KK21

[Sequence Listing Free Text]
SEQ ID NO: 1: Wild Type GmFAD21b
SEQ ID NO: 3: Mutant Type GmFAD21b
SEQ ID NO: 5: Mutant Type GmFAD21b
SEQ ID NO: 7: Synthetic DNA
SEQ ID NO: 8: Synthetic DNA
SEQ ID NO: 9: Synthetic DNA
SEQ ID NO: 10: Synthetic DNA
SEQ ID NO: 11: Synthetic DNA
SEQ ID NO: 12: Synthetic DNA
SEQ ID NO: 13: Synthetic DNA
SEQ ID NO: 14: Wild Type GmFAD21a
SEQ ID NO: 24: Synthetic DNA

[Sequence Listing]

The invention claimed is:

1. A modified soybean plant comprising:
    a high oleic acid content; and
    loss of function mutations in GmFAD2-1a and GmFAD2-1b genes,
    wherein the loss of function mutations introduced into GmFAD2-1gene of SEQ ID NO: 1 comprise Gly103 to Val103 and Thr189 to Pro189 of SEQ ID NO: 2, and
    wherein the loss of function mutation of the GmFAD2-1a gene is identical to that of the GmFAD2-1a gene of M23 or KK21 line.

2. The soybean plant according to claim 1, wherein the oleic content is 75% or more of the whole fatty acid content.

3. The soybean plant according to claim 1, comprising at least one of following features (a) to (e):
    (a) at least 60% of seeds of the soybean plant do not have a wrinkle on their surface;
    (b) the soybean plant does not produce linoleic acid, and wherein the amount of linoleic acid of the total fatty acid amount is 7% or less;
    (c) the soybean plant has an amount of beta-conglycinin content to the total storage protein amount that is not reduced compared to the wild type soybean plant, wherein the amount of beta-conglycinin content of the entire storage protein amount is 90% or more of that of the entire storage protein amount of the wild type soybean plant;
    (d) the soybean plant has a total storage protein amount that is not reduced compared to the wild type soybean plant, wherein the protein amount contained in the soybean plant is 90% or more of the total protein content of the wild type soybean plant;
    (e) the fertility of the soybean plant is not lowered compared to the wild type soybean plant, wherein the fertilization amount upon pollination between the soybean plants is 90% or more of the fertilization amount upon pollination between the wild type soybean plants,
    wherein the wild type soybean plants are selected from the group consisting of Bay, Murayutaka, and Fukuyutaka.

4. The soybean plant according to claim 1, having a gene that has a sequence of SEQ ID NO: 3 or SEQ ID NO: 5.

5. A method for manufacturing a modified soybean plant having a high oleic acid content, comprising:
    cross-mating the soybean plant recited in claim 1 with a second soybean plant as recited in claim 1, or another variety of soybean plant;
    screening the soybean plant having a mutation in GmFAD2-1a gene and a mutation in GmFAD2-1b gene;
    measuring a content of the oleic acid; and
    obtaining the modified soybean plant having a high oleic acid content.

6. A method of producing soybean oil comprising a step of extracting said soybean oil from a source, wherein the source is a soybean plant obtained by the method according to claim 5, or a processed material of said soybean plant, wherein the source has a high oleic acid content wherein loss of function mutations are introduced into GmFAD2-1a and GmFAD2-1b genes each encoding a ω-6 fatty acid desaturase.

* * * * *

UNITED STATES PATENT AND TRADEMARK OFFICE
CERTIFICATE OF CORRECTION

PATENT NO.        : 9,474,299 B2
APPLICATION NO.   : 13/379553
DATED             : October 25, 2016
INVENTOR(S)       : Toyoaki Anai It is certified that error appears in the above-identified patent and that said Letters Patent is hereby corrected as shown below:

In the Claims

Claim 1, at Column 51, Line 42, change "GmFAD2-1 gene" to --GmFAD2-1b gene--.

Signed and Sealed this
Ninth Day of May, 2017

Michelle K. Lee
*Director of the United States Patent and Trademark Office*

```
                              SEQUENCE LISTING

<160> NUMBER OF SEQ ID NOS: 24

<210> SEQ ID NO 1
<211> LENGTH: 1164
<212> TYPE: DNA
<213> ORGANISM: Glycine max L. Merr.
<220> FEATURE:
<221> NAME/KEY: CDS
<222> LOCATION: (1)..(1164)
<223> OTHER INFORMATION: Wild Type  GmFAD2-1b

<400> SEQUENCE: 1 atg ggt cta gca aag gaa aca ata atg gga ggt gga ggc cgt gtg gcc        48
Met Gly Leu Ala Lys Glu Thr Ile Met Gly Gly Gly Gly Arg Val Ala
1               5                  10                  15 aaa gtt gaa att cag cag aag aag cct ctc tca agg gtt cca aac aca        96
Lys Val Glu Ile Gln Gln Lys Lys Pro Leu Ser Arg Val Pro Asn Thr
                20                  25                  30 aag cca ccg ttc act gtt ggc caa ctc aag aaa gcc att cca ccg cac       144
Lys Pro Pro Phe Thr Val Gly Gln Leu Lys Lys Ala Ile Pro Pro His
            35                  40                  45 tgc ttt cag cgt tcc ctc ctc act tca ttg tcc tat gtt gtt tat gac       192
Cys Phe Gln Arg Ser Leu Leu Thr Ser Leu Ser Tyr Val Val Tyr Asp
        50                  55                  60 ctt tca ttg gct ttc att ttc tac att gcc acc acc tac ttc cac ctc       240
Leu Ser Leu Ala Phe Ile Phe Tyr Ile Ala Thr Thr Tyr Phe His Leu
65                  70                  75                  80 ctc cct cac ccc ttt tcc ctc att gca tgg cca atc tat tgg gtt ctc       288
Leu Pro His Pro Phe Ser Leu Ile Ala Trp Pro Ile Tyr Trp Val Leu
                85                  90                  95 caa ggt tgc att ctt act ggc gtg tgg gtg att gct cac gag tgt ggt       336
Gln Gly Cys Ile Leu Thr Gly Val Trp Val Ile Ala His Glu Cys Gly
            100                 105                 110 cac cat gcc ttc agc aag tac cca tgg gtt gat gat gtt gtg ggt ttg       384
His His Ala Phe Ser Lys Tyr Pro Trp Val Asp Asp Val Val Gly Leu
        115                 120                 125 acc gtt cac tca gca ctt tta gtc cct tat ttc tca tgg aaa ata agc       432
Thr Val His Ser Ala Leu Leu Val Pro Tyr Phe Ser Trp Lys Ile Ser
    130                 135                 140 cat cgc cgc cac cac tcc aac acg ggt tcc ctt gac cgt gat gaa gtg       480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg       528
Phe Val Pro Lys Pro Lys Ser Lys Val Ala Trp Tyr Thr Lys Tyr Leu
                165                 170                 175 aac aac cct cta gga agg gct gct tct ctt ctc atc aca ctc aca ata       576
Asn Asn Pro Leu Gly Arg Ala Ala Ser Leu Leu Ile Thr Leu Thr Ile
            180                 185                 190 ggg tgg cct ttg tat tta gcc ttc aat gtc tct ggc aga ccc tat gat       624
Gly Trp Pro Leu Tyr Leu Ala Phe Asn Val Ser Gly Arg Pro Tyr Asp
        195                 200                 205 ggt ttt gct agc cac tac cac cct tat gct ccc ata tat tca aat cgt       672
```

```
Gly Phe Ala Ser His Tyr His Pro Tyr Ala Pro Ile Tyr Ser Asn Arg
        210                 215                 220 gag agg ctt ttg atc tat gtc tct gat gtt gct ttg ttt tct gtg act      720
Glu Arg Leu Leu Ile Tyr Val Ser Asp Val Ala Leu Phe Ser Val Thr
225                 230                 235                 240 tac ttg ctc tac cgt gtt gca act atg aaa ggg ttg gtt tgg ctg cta      768
Tyr Leu Leu Tyr Arg Val Ala Thr Met Lys Gly Leu Val Trp Leu Leu
                245                 250                 255 tgt gtt tat ggg gtg cca ttg ctc att gtg aac ggt ttt ctt gtg acc      816
Cys Val Tyr Gly Val Pro Leu Leu Ile Val Asn Gly Phe Leu Val Thr
            260                 265                 270 atc aca tat ctg cag cac act cac tat gcc ttg cct cac tat gat tca      864
Ile Thr Tyr Leu Gln His Thr His Tyr Ala Leu Pro His Tyr Asp Ser
        275                 280                 285 tca gaa tgg gat tgg ctg agg ggt gct ttg gca act atg gac aga gat      912
Ser Glu Trp Asp Trp Leu Arg Gly Ala Leu Ala Thr Met Asp Arg Asp
290                 295                 300 tat ggg att ctg aac aag gtg ttt cac cac ata act gat act cat gtg      960
Tyr Gly Ile Leu Asn Lys Val Phe His His Ile Thr Asp Thr His Val
305                 310                 315                 320 gct cac cat ctt ttc tct aca atg cca cat tac cat gca acg gag gca     1008
Ala His His Leu Phe Ser Thr Met Pro His Tyr His Ala Thr Glu Ala
                325                 330                 335 acc aat gca atg aag cca ata ttg ggt gag tac tac cga ttt gat gac     1056
Thr Asn Ala Met Lys Pro Ile Leu Gly Glu Tyr Tyr Arg Phe Asp Asp
            340                 345                 350 aca cca ttt tac aag gca ctg tgg aga gaa gca aga gag tgc ctc tat     1104
Thr Pro Phe Tyr Lys Ala Leu Trp Arg Glu Ala Arg Glu Cys Leu Tyr
        355                 360                 365 gtg gag cca gat gaa gga aca tcc gag aag ggc gtg tat tgg tac agg     1152
Val Glu Pro Asp Glu Gly Thr Ser Glu Lys Gly Val Tyr Trp Tyr Arg
370                 375                 380 aac aag tat tga                                                      1164
Asn Lys Tyr
385

<210> SEQ ID NO 2
<211> LENGTH: 387
<212> TYPE: PRT
<213> ORGANISM: Glycine max L. Merr.

<400> SEQUENCE: 2

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Leu Ser Tyr Val Val Tyr Asp
        50                  55                  60

Leu Ser Leu Ala Phe Ile Phe Tyr Ile Ala Thr Thr Tyr Phe His Leu
65                  70                  75                  80

Leu Pro His Pro Phe Ser Leu Ile Ala Trp Pro Ile Tyr Trp Val Leu
                85                  90                  95

Gln Gly Cys Ile Leu Thr Gly Val Trp Val Ile Ala His Glu Cys Gly
            100                 105                 110

His His Ala Phe Ser Lys Tyr Pro Trp Val Asp Asp Val Val Gly Leu
        115                 120                 125
```

```
Thr Val His Ser Ala Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Thr Leu Thr Ile
            180                 185                 190

Gly Trp Pro Leu Tyr Leu Ala Phe Asn Val Ser Gly Arg Pro Tyr Asp
        195                 200                 205

Gly Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Leu Leu Tyr Arg Val Ala Thr Met Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Tyr Ala Leu Pro His Tyr Asp Ser
        275                 280                 285

Ser Glu Trp Asp Trp Leu Arg Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Thr Glu Ala
                325                 330                 335

Thr Asn Ala Met Lys Pro Ile Leu Gly Glu Tyr Tyr Arg Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
    370                 375                 380

Asn Lys Tyr
385

<210> SEQ ID NO 3
<211> LENGTH: 1164
<212> TYPE: DNA
<213> ORGANISM: Glycine max L. Merr.
<220> FEATURE:
<221> NAME/KEY: CDS
<222> LOCATION: (1)..(1164)
<223> OTHER INFORMATION: Mutant GmFAD2-1b

<400> SEQUENCE: 3 atg ggt cta gca aag gaa aca ata atg gga ggt gga ggc cgt gtg gcc      48
Met Gly Leu Ala Lys Glu Thr Ile Met Gly Gly Gly Gly Arg Val Ala
1               5                   10                  15 aaa gtt gaa att cag cag aag aag cct ctc tca agg gtt cca aac aca      96
Lys Val Glu Ile Gln Gln Lys Lys Pro Leu Ser Arg Val Pro Asn Thr
            20                  25                  30 aag cca ccg ttc act gtt ggc caa ctc aag aaa gcc att cca ccg cac     144
Lys Pro Pro Phe Thr Val Gly Gln Leu Lys Lys Ala Ile Pro Pro His
        35                  40                  45 tgc ttt cag cgt tcc ctc ctc act tca ttg tcc tat gtt gtt tat gac     192
Cys Phe Gln Arg Ser Leu Leu Thr Ser Leu Ser Tyr Val Val Tyr Asp
    50                  55                  60
```

```
ctt tca ttg gct ttc att ttc tac att gcc acc acc tac ttc cac ctc      240
Leu Ser Leu Ala Phe Ile Phe Tyr Ile Ala Thr Thr Tyr Phe His Leu
 65                  70                  75                  80 ctc cct cac ccc ttt tcc ctc att gca tgg cca atc tat tgg gtt ctc      288
Leu Pro His Pro Phe Ser Leu Ile Ala Trp Pro Ile Tyr Trp Val Leu
                     85                  90                  95 caa ggt tgc att ctt act gtc gtg tgg gtt att gct cac gag tgt ggt      336
Gln Gly Cys Ile Leu Thr Val Val Trp Val Ile Ala His Glu Cys Gly
                100                 105                 110 cac cat gcc ttc agc aag tac cca tgg gtt gat gat gtt gtg ggt ttg      384
His His Ala Phe Ser Lys Tyr Pro Trp Val Asp Asp Val Val Gly Leu
            115                 120                 125 acc gtt cac tca gca ctt tta gtc cct tat ttc tca tgg aaa ata agc      432
Thr Val His Ser Ala Leu Leu Val Pro Tyr Phe Ser Trp Lys Ile Ser
        130                 135                 140 cat cgc cgc cac cac tcc aac acg ggt tcc ctt gac cgt gat gaa gtg      480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg      528
Phe Val Pro Lys Pro Lys Ser Lys Val Ala Trp Tyr Thr Lys Tyr Leu
                165                 170                 175 aac aac cct cta gga agg gct gct tct ctt ctc atc aca ctc aca ata      576
Asn Asn Pro Leu Gly Arg Ala Ala Ser Leu Leu Ile Thr Leu Thr Ile
                180                 185                 190 ggg tgg cct ttg tat tta gcc ttc aat gtc tct ggc aga ccc tat gat      624
Gly Trp Pro Leu Tyr Leu Ala Phe Asn Val Ser Gly Arg Pro Tyr Asp
            195                 200                 205 ggt ttt gct agc cac tac cac cct tat gct ccc ata tat tca aat cgt      672
Gly Phe Ala Ser His Tyr His Pro Tyr Ala Pro Ile Tyr Ser Asn Arg
        210                 215                 220 gag agg ctt ttg atc tat gtc tct gat gtt gct ttg ttt tct gtg act      720
Glu Arg Leu Leu Ile Tyr Val Ser Asp Val Ala Leu Phe Ser Val Thr
225                 230                 235                 240 tac ttg ctc tac cgt gtt gca act atg aaa ggg ttg gtt tgg ctg cta      768
Tyr Leu Leu Tyr Arg Val Ala Thr Met Lys Gly Leu Val Trp Leu Leu
                245                 250                 255 tgt gtt tat ggg gtg cca ttg ctc att gtg aac ggt ttt ctt gtg acc      816
Cys Val Tyr Gly Val Pro Leu Leu Ile Val Asn Gly Phe Leu Val Thr
                260                 265                 270 atc aca tat ctg cag cac act cac tat gcc ttg cct cac tat gat tca      864
Ile Thr Tyr Leu Gln His Thr His Tyr Ala Leu Pro His Tyr Asp Ser
            275                 280                 285 tca gaa tgg gat tgg ctg agg ggt gct ttg gca act atg gac aga gat      912
Ser Glu Trp Asp Trp Leu Arg Gly Ala Leu Ala Thr Met Asp Arg Asp
        290                 295                 300 tat ggg att ctg aac aag gtg ttt cac cac ata act gat act cat gtg      960
Tyr Gly Ile Leu Asn Lys Val Phe His His Ile Thr Asp Thr His Val
305                 310                 315                 320 gct cac cat ctt ttc tct aca atg cca cat tac cat gca acg gag gca     1008
Ala His His Leu Phe Ser Thr Met Pro His Tyr His Ala Thr Glu Ala
                325                 330                 335 acc aat gca atg aag cca ata ttg ggt gag tac tac cga ttt gat gac     1056
Thr Asn Ala Met Lys Pro Ile Leu Gly Glu Tyr Tyr Arg Phe Asp Asp
                340                 345                 350 aca cca ttt tac aag gca ctg tgg aga gaa gca aga gag tgc ctc tat     1104
Thr Pro Phe Tyr Lys Ala Leu Trp Arg Glu Ala Arg Glu Cys Leu Tyr
            355                 360                 365 gtg gag cca gat gaa gga aca tcc gag aag ggc gtg tat tgg tac agg     1152
Val Glu Pro Asp Glu Gly Thr Ser Glu Lys Gly Val Tyr Trp Tyr Arg
370                 375                 380
```

```
aac aag tat tga                                                    1164
Asn Lys Tyr
385
```

<210> SEQ ID NO 4
<211> LENGTH: 387
<212> TYPE: PRT
<213> ORGANISM: Glycine max L. Merr.

<400> SEQUENCE: 4

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
            20                  25                  30

Lys Pro Pro Phe Thr Val Gly Gln Leu Lys Lys Ala Ile Pro Pro His
                35                  40                  45

Cys Phe Gln Arg Ser Leu Leu Thr Ser Leu Ser Tyr Val Val Tyr Asp
    50                  55                  60

Leu Ser Leu Ala Phe Ile Phe Tyr Ile Ala Thr Thr Tyr Phe His Leu
65                  70                  75                  80

Leu Pro His Pro Phe Ser Leu Ile Ala Trp Pro Ile Tyr Trp Val Leu
                85                  90                  95

Gln Gly Cys Ile Leu Thr Val Val Trp Val Ile Ala His Glu Cys Gly
            100                 105                 110

His His Ala Phe Ser Lys Tyr Pro Trp Val Asp Val Val Gly Leu
        115                 120                 125

Thr Val His Ser Ala Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Thr Leu Thr Ile
            180                 185                 190

Gly Trp Pro Leu Tyr Leu Ala Phe Asn Val Ser Gly Arg Pro Tyr Asp
        195                 200                 205

Gly Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Leu Leu Tyr Arg Val Ala Thr Met Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Tyr Ala Leu Pro His Tyr Asp Ser
        275                 280                 285

Ser Glu Trp Asp Trp Leu Arg Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Thr Glu Ala
                325                 330                 335

Thr Asn Ala Met Lys Pro Ile Leu Gly Glu Tyr Tyr Arg Phe Asp Asp
            340                 345                 350

```
Thr Pro Phe Tyr Lys Ala Leu Trp Arg Glu Ala Arg Glu Cys Leu Tyr
            355                 360                 365

Val Glu Pro Asp Glu Gly Thr Ser Glu Lys Gly Val Tyr Trp Tyr Arg
        370                 375                 380

Asn Lys Tyr
385

<210> SEQ ID NO 5
<211> LENGTH: 1164
<212> TYPE: DNA
<213> ORGANISM: Glycine max L. Merr.
<220> FEATURE:
<221> NAME/KEY: CDS
<222> LOCATION: (1)..(1164)
<223> OTHER INFORMATION: Mutant GmFAD2-1b

<400> SEQUENCE: 5 atg ggt cta gca aag gaa aca ata atg gga ggt gga ggc cgt gtg gcc        48
Met Gly Leu Ala Lys Glu Thr Ile Met Gly Gly Gly Gly Arg Val Ala
1               5                   10                  15 aaa gtt gaa att cag cag aag aag cct ctc tca agg gtt cca aac aca        96
Lys Val Glu Ile Gln Gln Lys Lys Pro Leu Ser Arg Val Pro Asn Thr
                20                  25                  30 aag cca ccg ttc act gtt ggc caa ctc aag aaa gcc att cca ccg cac       144
Lys Pro Pro Phe Thr Val Gly Gln Leu Lys Lys Ala Ile Pro Pro His
            35                  40                  45 tgc ttt cag cgt tcc ctc ctc act tca ttg tcc tat gtt gtt tat gac       192
Cys Phe Gln Arg Ser Leu Leu Thr Ser Leu Ser Tyr Val Val Tyr Asp
    50                  55                  60 ctt tca ttg gct ttc att ttc tac att gcc acc acc tac ttc cac ctc       240
Leu Ser Leu Ala Phe Ile Phe Tyr Ile Ala Thr Thr Tyr Phe His Leu
65                  70                  75                  80 ctc cct cac ccc ttt tcc ctc att gca tgg cca atc tat tgg gtt ctc       288
Leu Pro His Pro Phe Ser Leu Ile Ala Trp Pro Ile Tyr Trp Val Leu
                85                  90                  95 caa ggt tgc att ctt act ggc gtg tgg gtg att gct cac gag tgt ggt       336
Gln Gly Cys Ile Leu Thr Gly Val Trp Val Ile Ala His Glu Cys Gly
                100                 105                 110 cac cat gcc ttc agc aag tac cca tgg gtt gat gat gtt gtg ggt ttg       384
His His Ala Phe Ser Lys Tyr Pro Trp Val Asp Asp Val Val Gly Leu
            115                 120                 125 acc gtt cac tca gca ctt tta gtc cct tat ttc tca tgg aaa ata agc       432
Thr Val His Ser Ala Leu Leu Val Pro Tyr Phe Ser Trp Lys Ile Ser
    130                 135                 140 cat cgc cgc cac cac tcc aac acg ggt tcc ctt gac cgt gat gaa gtg       480
His Arg Arg His His Ser Asn Thr Gly Ser Leu Asp Arg Asp Glu Val
145                 150                 155                 160 ttt gtc cca aaa cca aaa tcc aaa gtt gca tgg tac acc aag tac ctg       528
Phe Val Pro Lys Pro Lys Ser Lys Val Ala Trp Tyr Thr Lys Tyr Leu
                165                 170                 175 aac aac cct cta gga agg gct gct tct ctt ctc atc cca ctc aca ata       576
Asn Asn Pro Leu Gly Arg Ala Ala Ser Leu Leu Ile Pro Leu Thr Ile
                180                 185                 190 ggg tgg cct ttg tat tta gcc ttc aat gtc tct ggc aga ccc tat gat       624
Gly Trp Pro Leu Tyr Leu Ala Phe Asn Val Ser Gly Arg Pro Tyr Asp
            195                 200                 205 ggt ttt gct agc cac tac cac cct tat gct ccc ata tat tca aat cgt       672
Gly Phe Ala Ser His Tyr His Pro Tyr Ala Pro Ile Tyr Ser Asn Arg
    210                 215                 220 gag agg ctt ttg atc tat gtc tct gat gtt gct ttg ttt tct gtg act       720
Glu Arg Leu Leu Ile Tyr Val Ser Asp Val Ala Leu Phe Ser Val Thr
```

```
                    225                 230                 235                 240
tac ttg ctc tac cgt gtt gca act atg aaa ggg ttg gtt tgg ctg cta      768
Tyr Leu Leu Tyr Arg Val Ala Thr Met Lys Gly Leu Val Trp Leu Leu
                    245                 250                 255 tgt gtt tat ggg gtg cca ttg ctc att gtg aac ggt ttt ctt gtg acc      816
Cys Val Tyr Gly Val Pro Leu Leu Ile Val Asn Gly Phe Leu Val Thr
                260                 265                 270 atc aca tat ctg cag cac act cac tat gcc ttg cct cac tat gat tca      864
Ile Thr Tyr Leu Gln His Thr His Tyr Ala Leu Pro His Tyr Asp Ser
            275                 280                 285 tca gaa tgg gat tgg ctg agg ggt gct ttg gca act atg gac aga gat      912
Ser Glu Trp Asp Trp Leu Arg Gly Ala Leu Ala Thr Met Asp Arg Asp
        290                 295                 300 tat ggg att ctg aac aag gtg ttt cac cac ata act gat act cat gtg      960
Tyr Gly Ile Leu Asn Lys Val Phe His His Ile Thr Asp Thr His Val
305                 310                 315                 320 gct cac cat ctt ttc tct aca atg cca cat tac cat gca acg gag gca     1008
Ala His His Leu Phe Ser Thr Met Pro His Tyr His Ala Thr Glu Ala
                325                 330                 335 acc aat gca atg aag cca ata ttg ggt gag tac tac cga ttt gat gac     1056
Thr Asn Ala Met Lys Pro Ile Leu Gly Glu Tyr Tyr Arg Phe Asp Asp
            340                 345                 350 aca cca ttt tac aag gca ctg tgg aga gaa gca aga gag tgc ctc tat     1104
Thr Pro Phe Tyr Lys Ala Leu Trp Arg Glu Ala Arg Glu Cys Leu Tyr
        355                 360                 365 gtg gag cca gat gaa gga aca tcc gag aag ggc gtg tat tgg tac agg     1152
Val Glu Pro Asp Glu Gly Thr Ser Glu Lys Gly Val Tyr Trp Tyr Arg
370                 375                 380 aac aag tat tga                                                      1164
Asn Lys Tyr
385

<210> SEQ ID NO 6
<211> LENGTH: 387
<212> TYPE: PRT
<213> ORGANISM: Glycine max L. Merr.

<400> SEQUENCE: 6

Met Gly Leu Ala Lys Glu Thr Ile Met Gly Gly Gly Arg Val Ala
1               5                   10                  15

Lys Val Glu Ile Gln Gln Lys Lys Pro Leu Ser Arg Val Pro Asn Thr
                20                  25                  30

Lys Pro Pro Phe Thr Val Gly Gln Leu Lys Lys Ala Ile Pro Pro His
            35                  40                  45

Cys Phe Gln Arg Ser Leu Leu Thr Ser Leu Ser Tyr Val Val Tyr Asp
        50                  55                  60

Leu Ser Leu Ala Phe Ile Phe Tyr Ile Ala Thr Thr Tyr Phe His Leu
65                  70                  75                  80

Leu Pro His Pro Phe Ser Leu Ile Ala Trp Pro Ile Tyr Trp Val Leu
                85                  90                  95

Gln Gly Cys Ile Leu Thr Gly Val Trp Val Ile Ala His Glu Cys Gly
                100                 105                 110

His His Ala Phe Ser Lys Tyr Pro Trp Val Asp Asp Val Val Gly Leu
            115                 120                 125

Thr Val His Ser Ala Leu Leu Val Pro Tyr Phe Ser Trp Lys Ile Ser
        130                 135                 140

His Arg Arg His His Ser Asn Thr Gly Ser Leu Asp Arg Asp Glu Val
145                 150                 155                 160
```

Phe Val Pro Lys Pro Lys Ser Lys Val Ala Trp Tyr Thr Lys Tyr Leu
                165                 170                 175

Asn Asn Pro Leu Gly Arg Ala Ala Ser Leu Leu Ile Pro Leu Thr Ile
            180                 185                 190

Gly Trp Pro Leu Tyr Leu Ala Phe Asn Val Ser Gly Arg Pro Tyr Asp
        195                 200                 205

Gly Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Leu Leu Tyr Arg Val Ala Thr Met Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Tyr Ala Leu Pro His Tyr Asp Ser
        275                 280                 285

Ser Glu Trp Asp Trp Leu Arg Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro Tyr His Ala Thr Glu Ala
                325                 330                 335

Thr Asn Ala Met Lys Pro Ile Leu Gly Glu Tyr Tyr Arg Phe Asp Asp
            340                 345                 350

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
    370                 375                 380

Asn Lys Tyr
385

<210> SEQ ID NO 7
<211> LENGTH: 25
<212> TYPE: DNA
<213> ORGANISM: Artificial
<220> FEATURE:
<223> OTHER INFORMATION: Synthetic DNA

<400> SEQUENCE: 7
attgatagcc cctccgttcc caaga                                        25

<210> SEQ ID NO 8
<211> LENGTH: 26
<212> TYPE: DNA
<213> ORGANISM: Artificial
<220> FEATURE:
<223> OTHER INFORMATION: Synthetic DNA

<400> SEQUENCE: 8
atacacacaa agtcattacg cggcaa                                       26

<210> SEQ ID NO 9
<211> LENGTH: 25
<212> TYPE: DNA
<213> ORGANISM: Artificial
<220> FEATURE:
<223> OTHER INFORMATION: Synthetic DNA

<400> SEQUENCE: 9

```
attgatagcc cctccgttcc caaga                                              25
```

<210> SEQ ID NO 10
<211> LENGTH: 26
<212> TYPE: DNA
<213> ORGANISM: Artificial
<220> FEATURE:
<223> OTHER INFORMATION: Synthetic DNA

<400> SEQUENCE: 10

```
attgtgagtg tgacgagaag agaaac                                             26
```

<210> SEQ ID NO 11
<211> LENGTH: 31
<212> TYPE: DNA
<213> ORGANISM: Artificial
<220> FEATURE:
<223> OTHER INFORMATION: Synthetic DNA

<400> SEQUENCE: 11

```
gggtctagca aggaaacaa caatgggagg t                                        31
```

<210> SEQ ID NO 12
<211> LENGTH: 26
<212> TYPE: DNA
<213> ORGANISM: Artificial
<220> FEATURE:
<223> OTHER INFORMATION: Synthetic DNA

<400> SEQUENCE: 12

```
tctgtcactt ccctccattc attttg                                             26
```

<210> SEQ ID NO 13
<211> LENGTH: 33
<212> TYPE: DNA
<213> ORGANISM: Artificial
<220> FEATURE:
<223> OTHER INFORMATION: Synthetic DNA

<400> SEQUENCE: 13

```
gggaagctta tacacaaagt cattacgcgg caa                                     33
```

<210> SEQ ID NO 14
<211> LENGTH: 1164
<212> TYPE: DNA
<213> ORGANISM: Glycine max L. Merr.
<220> FEATURE:
<221> NAME/KEY: CDS
<222> LOCATION: (1)..(1164)
<223> OTHER INFORMATION: Wild Type GmFAD2-1a

<400> SEQUENCE: 14

```
atg ggt cta gca aag gaa aca aca atg gga ggt aga ggt cgt gtg gcc          48
Met Gly Leu Ala Lys Glu Thr Thr Met Gly Gly Arg Gly Arg Val Ala
1               5                   10                  15 aaa gtg gaa gtt caa ggg aag aag cct ctc tca agg gtt cca aac aca          96
Lys Val Glu Val Gln Gly Lys Lys Pro Leu Ser Arg Val Pro Asn Thr
            20                  25                  30 aag cca cca ttc act gtt ggc caa ctc aag aaa gca att cca cca cac         144
Lys Pro Pro Phe Thr Val Gly Gln Leu Lys Lys Ala Ile Pro Pro His
        35                  40                  45 tgc ttt cag cgc tcc ctc ctc act tca ttc tcc tat gtt gtt tat gac         192
Cys Phe Gln Arg Ser Leu Leu Thr Ser Phe Ser Tyr Val Val Tyr Asp
    50                  55                  60
```

```
ctt tca ttt gcc ttc att ttc tac att gcc acc acc tac ttc cac ctc         240
Leu Ser Phe Ala Phe Ile Phe Tyr Ile Ala Thr Thr Tyr Phe His Leu
65                  70                  75                  80 ctt cct caa ccc ttt tcc ctc att gca tgg cca atc tat tgg gtt ctc         288
Leu Pro Gln Pro Phe Ser Leu Ile Ala Trp Pro Ile Tyr Trp Val Leu
                85                  90                  95 caa ggt tgc ctt ctc act ggt gtg tgg gtt att gct cac gag tgt ggt         336
Gln Gly Cys Leu Leu Thr Gly Val Trp Val Ile Ala His Glu Cys Gly
            100                 105                 110 cac cat gcc ttc agc aag tac caa tgg gtt gat gat gtt gtg ggt ttg         384
His His Ala Phe Ser Lys Tyr Gln Trp Val Asp Asp Val Val Gly Leu
            115                 120                 125 acc ctt cac tca aca ctt tta gtc cct tat ttc tca tgg aaa ata agc         432
Thr Leu His Ser Thr Leu Leu Val Pro Tyr Phe Ser Trp Lys Ile Ser
130                 135                 140 cat cgc cgc cat cac tcc aac aca ggt tcc ctt gac cgt gat gaa gtg         480
His Arg Arg His His Ser Asn Thr Gly Ser Leu Asp Arg Asp Glu Val
145                 150                 155                 160 ttt gtc cca aaa cca aaa tcc aaa gtt gca tgg ttt tcc aag tac tta         528
Phe Val Pro Lys Pro Lys Ser Lys Val Ala Trp Phe Ser Lys Tyr Leu
                165                 170                 175 aac aac cct cta gga agg gct gtt tct ctt ctc gtc aca ctc aca ata         576
Asn Asn Pro Leu Gly Arg Ala Val Ser Leu Leu Val Thr Leu Thr Ile
            180                 185                 190 ggg tgg cct atg tat tta gcc ttc aat gtc tct ggt aga ccc tat gat         624
Gly Trp Pro Met Tyr Leu Ala Phe Asn Val Ser Gly Arg Pro Tyr Asp
            195                 200                 205 agt ttt gca agc cac tac cac cct tat gct ccc ata tat tct aac cgt         672
Ser Phe Ala Ser His Tyr His Pro Tyr Ala Pro Ile Tyr Ser Asn Arg
210                 215                 220 gag agg ctt ctg atc tat gtc tct gat gtt gct ttg ttt tct gtg act         720
Glu Arg Leu Leu Ile Tyr Val Ser Asp Val Ala Leu Phe Ser Val Thr
225                 230                 235                 240 tac tct ctc tac cgt gtt gca acc ctg aaa ggg ttg gtt tgg ctg cta         768
Tyr Ser Leu Tyr Arg Val Ala Thr Leu Lys Gly Leu Val Trp Leu Leu
                245                 250                 255 tgt gtt tat ggg gtg cct ttg ctc att gtg aac ggt ttt ctt gtg act         816
Cys Val Tyr Gly Val Pro Leu Leu Ile Val Asn Gly Phe Leu Val Thr
            260                 265                 270 atc aca tat ttg cag cac aca cac ttt gcc ttg cct cat tac gat tca         864
Ile Thr Tyr Leu Gln His Thr His Phe Ala Leu Pro His Tyr Asp Ser
            275                 280                 285 tca gaa tgg gac tgg ctg aag gga gct ttg gca act atg gac aga gat         912
Ser Glu Trp Asp Trp Leu Lys Gly Ala Leu Ala Thr Met Asp Arg Asp
            290                 295                 300 tat ggg att ctg aac aag gtg ttt cat cac ata act gat act cat gtg         960
Tyr Gly Ile Leu Asn Lys Val Phe His His Ile Thr Asp Thr His Val
305                 310                 315                 320 gct cac cat ctc ttc tct aca atg cca cat tac cat gca atg gag gca        1008
Ala His His Leu Phe Ser Thr Met Pro His Tyr His Ala Met Glu Ala
                325                 330                 335 acc aat gca atc aag cca ata ttg ggt gag tac tac caa ttt gat gac        1056
Thr Asn Ala Ile Lys Pro Ile Leu Gly Glu Tyr Tyr Gln Phe Asp Asp
            340                 345                 350 aca cca ttt tac aag gca ctg tgg aga gaa gcg aga gag tgc ctc tat        1104
Thr Pro Phe Tyr Lys Ala Leu Trp Arg Glu Ala Arg Glu Cys Leu Tyr
            355                 360                 365 gtg gag cca gat gaa gga aca tcc gag aag ggc gtg tat tgg tac agg        1152
Val Glu Pro Asp Glu Gly Thr Ser Glu Lys Gly Val Tyr Trp Tyr Arg
370                 375                 380
```

```
aac aag tat tga                                                    1164
Asn Lys Tyr
385
```

<210> SEQ ID NO 15
<211> LENGTH: 387
<212> TYPE: PRT
<213> ORGANISM: Glycine max L. Merr.

<400> SEQUENCE: 15

```
Met Gly Leu Ala Lys Glu Thr Thr Met Gly Arg Gly Arg Val Ala
1               5                  10                  15

Lys Val Glu Val Gln Gly Lys Lys Pro Leu Ser Arg Val Pro Asn Thr
            20                  25                  30

Lys Pro Pro Phe Thr Val Gly Gln Leu Lys Lys Ala Ile Pro Pro His
        35                  40                  45

Cys Phe Gln Arg Ser Leu Leu Thr Ser Phe Ser Tyr Val Val Tyr Asp
    50                  55                  60

Leu Ser Phe Ala Phe Ile Phe Tyr Ile Ala Thr Thr Tyr Phe His Leu
65                  70                  75                  80

Leu Pro Gln Pro Phe Ser Leu Ile Ala Trp Pro Ile Tyr Trp Val Leu
                85                  90                  95

Gln Gly Cys Leu Leu Thr Gly Val Trp Val Ile Ala His Glu Cys Gly
            100                 105                 110

His His Ala Phe Ser Lys Tyr Gln Trp Val Asp Asp Val Val Gly Leu
        115                 120                 125

Thr Leu His Ser Thr Leu Leu Val Pro Tyr Phe Ser Trp Lys Ile Ser
    130                 135                 140

His Arg Arg His His Ser Asn Thr Gly Ser Leu Asp Arg Asp Glu Val
145                 150                 155                 160

Phe Val Pro Lys Pro Lys Ser Lys Val Ala Trp Phe Ser Lys Tyr Leu
                165                 170                 175

Asn Asn Pro Leu Gly Arg Ala Val Ser Leu Leu Val Thr Leu Thr Ile
            180                 185                 190

Gly Trp Pro Met Tyr Leu Ala Phe Asn Val Ser Gly Arg Pro Tyr Asp
        195                 200                 205

Ser Phe Ala Ser His Tyr His Pro Tyr Ala Pro Ile Tyr Ser Asn Arg
    210                 215                 220

Glu Arg Leu Leu Ile Tyr Val Ser Asp Val Ala Leu Phe Ser Val Thr
225                 230                 235                 240

Tyr Ser Leu Tyr Arg Val Ala Thr Leu Lys Gly Leu Val Trp Leu Leu
                245                 250                 255

Cys Val Tyr Gly Val Pro Leu Leu Ile Val Asn Gly Phe Leu Val Thr
            260                 265                 270

Ile Thr Tyr Leu Gln His Thr His Phe Ala Leu Pro His Tyr Asp Ser
        275                 280                 285

Ser Glu Trp Asp Trp Leu Lys Gly Ala Leu Ala Thr Met Asp Arg Asp
    290                 295                 300

Tyr Gly Ile Leu Asn Lys Val Phe His His Ile Thr Asp Thr His Val
305                 310                 315                 320

Ala His His Leu Phe Ser Thr Met Pro His Tyr His Ala Met Glu Ala
                325                 330                 335

Thr Asn Ala Ile Lys Pro Ile Leu Gly Glu Tyr Gln Phe Asp Asp
            340                 345                 350
```

-continued

Thr Pro Phe Tyr Lys Ala Leu Trp Arg Glu Ala Arg Glu Cys Leu Tyr
        355                 360                 365

Val Glu Pro Asp Glu Gly Thr Ser Glu Lys Gly Val Tyr Trp Tyr Arg
    370                 375                 380

Asn Lys Tyr
385

<210> SEQ ID NO 16
<211> LENGTH: 22
<212> TYPE: PRT
<213> ORGANISM: Glycine max L. Merr.

<400> SEQUENCE: 16

Leu Ser Tyr Val Val Tyr Asp Leu Ser Leu Ala Phe Ile Phe Tyr Ile
1               5                   10                  15

Ala Thr Thr Tyr Phe His
            20

<210> SEQ ID NO 17
<211> LENGTH: 21
<212> TYPE: PRT
<213> ORGANISM: Glycine max L. Merr.

<400> SEQUENCE: 17

Ile Ala Trp Pro Ile Tyr Trp Val Leu Gln Gly Cys Ile Leu Thr Gly
1               5                   10                  15

Val Trp Val Ile Ala
            20

<210> SEQ ID NO 18
<211> LENGTH: 15
<212> TYPE: PRT
<213> ORGANISM: Glycine max L. Merr.

<400> SEQUENCE: 18

Leu Gly Arg Ala Ala Ser Leu Leu Ile Thr Leu Thr Ile Gly Trp
1               5                   10                  15

<210> SEQ ID NO 19
<211> LENGTH: 23
<212> TYPE: PRT
<213> ORGANISM: Glycine max L. Merr.

<400> SEQUENCE: 19

Ile Tyr Val Ser Asp Val Ala Leu Phe Ser Val Thr Tyr Leu Leu Tyr
1               5                   10                  15

Arg Val Ala Thr Met Lys Gly
            20

<210> SEQ ID NO 20
<211> LENGTH: 24
<212> TYPE: PRT
<213> ORGANISM: Glycine max L. Merr.

<400> SEQUENCE: 20

Trp Leu Leu Cys Val Tyr Gly Val Pro Leu Leu Ile Val Asn Gly Phe
1               5                   10                  15

Leu Val Thr Ile Thr Tyr Leu Gln
            20

<210> SEQ ID NO 21
<211> LENGTH: 6

```
<212> TYPE: PRT
<213> ORGANISM: Glycine max L. Merr.

<400> SEQUENCE: 21

His Glu Cys Gly His His
1               5

<210> SEQ ID NO 22
<211> LENGTH: 9
<212> TYPE: PRT
<213> ORGANISM: Glycine max L. Merr.

<400> SEQUENCE: 22

Trp Lys Ile Ser His Arg Arg His His
1               5

<210> SEQ ID NO 23
<211> LENGTH: 8
<212> TYPE: PRT
<213> ORGANISM: Glycine max L. Merr.

<400> SEQUENCE: 23

His Val Ala His His Leu Phe Ser
1               5

<210> SEQ ID NO 24
<211> LENGTH: 27
<212> TYPE: DNA
<213> ORGANISM: Artificial
<220> FEATURE:
<223> OTHER INFORMATION: Synthetic DNA

<400> SEQUENCE: 24
atattacaca ttcagcaaaa caactga                                            27
```